United States Patent [19]

Kobayashi et al.

[11] Patent Number: 5,536,737
[45] Date of Patent: Jul. 16, 1996

[54] COMPOUND HAVING PROLYL ENDOPEPTIDASE INHIBITORY ACTIVITY AND PHARMACEUTICAL USE THEREOF

[75] Inventors: Koji Kobayashi; Minoru Akamatsu; Shinji Yata; Hiroyuki Abe; Katsuo Toide; Motohiro Kogayu; Itsuo Uchida, all of Takatsuki, Japan

[73] Assignee: Japan Tobacco Inc., Tokyo, Japan

[21] Appl. No.: 446,592

[22] PCT Filed: Nov. 17, 1993

[86] PCT No.: PCT/JP93/01687

§ 371 Date: May 24, 1995

§ 102(e) Date: May 24, 1995

[87] PCT Pub. No.: WO94/12474

PCT Pub. Date: Nov. 17, 1993

[30] Foreign Application Priority Data

Nov. 20, 1992 [JP] Japan .................................... 4-333899
Apr. 16, 1993 [JP] Japan .................................... 5-089775

[51] Int. Cl.⁶ .................... C07D 403/06; C07D 417/06; A61K 31/40; A61K 31/425

[52] U.S. Cl. .................... 514/365; 514/422; 548/200; 548/518

[58] Field of Search .................... 548/200, 518; 514/365, 422

[56] References Cited

FOREIGN PATENT DOCUMENTS 5-201970  8/1993  Japan .
9313065   7/1993  WIPO .

OTHER PUBLICATIONS

Database WPI, Derwent Publications Ltd., Week 9337, Abstract of JP-A-5 201 970.

*Primary Examiner*—Robert Gerstl
*Attorney, Agent, or Firm*—Wenderoth, Lind & Ponack

[57] ABSTRACT

Compounds of the formula

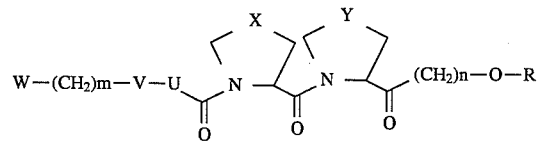

wherein R is a hydrogen atom or an acyl; U is —O—, —CHR¹— or —NR²— wherein R¹ is a hydrogen atom or a hetero ring, and R² is a hydrogen atom or a lower alkoxycarbonyl lower alkyl; V is —O—, —S—, —CHR³— or —NR⁴— wherein R³ is a hydrogen atom or a lower alkoxycarbonyl, and R⁴ is a hydrogen atom, a lower alkyl or an acyl; W is methyl, a hetero ring or optionally substituted phenyl; X and Y are the same or different and each is —CH₂— or —S—; m is an integer of 0 to 6; and n is an integer of 1 to 4, and pharmaceutically acceptable salts thereof.

The compounds of the present invention have specifically strong inhibitory activity against prolyl endopeptidase, and suppress decomposition and inactivation of TRH, substance P, neurotensin, vasopressin and the like. Accordingly, the compounds can be used for the prophylaxis and/or treatment of dementia and amnesia including Alzheimer's disease.

10 Claims, No Drawings

COMPOUND HAVING PROLYL ENDOPEPTIDASE INHIBITORY ACTIVITY AND PHARMACEUTICAL USE THEREOF

This application is a 371 of PCT/JP93/01687 filed Nov. 17, 1993.

TECHNICAL FIELD

The present invention relates to a novel compound having a prolyl endopeptidase inhibitory activity, which is used in the medical field.

BACKGROUND ART

With the advent of an aging society, the problem of the medical care of senile citizens has been drawing attention. Above all, senile dementia has become a serious social problem, and many developments have been made in an attempt to provide new pharmaceuticals to cope with the situation. The conventional therapeutic agents for amnesia and dementia have been named obscurely as cerebral circulation-improving agents, cerebral metabolism activator or cerebral function-improving agents according to their action mechanisms. While they are effective for the improvement of peripheral symptoms such as depression, emotional disturbances, abnormal behavior, etc., they do not show definite effects on the central symptoms of dementia, such as memory disorder, disorientation and the like. Thus, the development of pharmaceutical agents which can provide dependable action and effects on these symptoms is desired.

Prolyl endopeptidase; EC, 3.4.21.26 is known to act on peptides containing proline and to specifically cleave the carboxyl side of the proline. Further, this enzyme vasopressin which is presumably concerned with learning and memory process, to decompose and inactivate same.

In view of the foregoing findings, a compound possessing specific inhibitory activity on this enzyme is expected to suppress decomposition and inactivation of vasopressin, etc., thus suggesting a potential application thereof to the treatment and prevention of amnesia and dementia, as a pharmaceutical agent which directly acts on the central symptoms of dementia [see Seikagaku, 55, 831 (1983); FOLIA PHARMACOL. JAPON, 89, 243 (1987); and J. Pharmacobio-Dyn., 10, 730 (1987)]. It is also expected that such a compound suppresses decomposition and inactivation of hormones and neurotransmitters such as TRH, substance P, neurotensin etc., thereby improving various symptoms caused by the decomposition and inactivation of these substances. Recent studies have revealed that beta amyloid protein plays a substantial and important role in the onset of Alzheimer's disease by the neorotoxic action thereof in in vitro and in vivo tests. Based on the hypothesis that prolyl endopeptidase is an enzyme for cleaving out a beta amyloid from an amyloid precursor protein (FEBS Lett., 260, 131–134 (1990)] and the experimental fact that the neurotoxic action of beta amyloid protein is suppressed by substance P [Proc. Natl. Acad. Sci. USA, 88, 7247–7251 (1991)], a prolyl endopeptidase inhibitor is considered to become an effective medicine for Alzheimer's disease.

There have been conventionally attempted to develop prolyl endopeptidase inhibitors and various proline derivatives are described and disclosed in, for example, Japanese Patent Unexamined Publication Nos. 148467/1987, 42475/1989, 6263/1989, 230578/1989 and 28149/1990.

DISCLOSURE OF THE INVENTION

An object of the present invention is to provide a novel compound having a specific and strong prolyl endopeptidase inhibitory activity.

Another object of the present invention is to provide a pharmaceutical composition useful as a prolyl endopeptidase inhibitor, specifically a pharmaceutical agent which directly acts on the central symptoms of dementia, i.e., a medicament effective for the prophylaxis and treatment of amnesia and dementia. The compound of the present invention is also expected to be useful as a therapeutic agent for Alzheimer's disease.

Based on the aforementioned findings, the present inventors have conducted intensive studies in an attempt to find a compound having, as a fragment, a dipeptide residue formed by amino acids, particularly by proline residue and thioproline residue in combination, and which specifically and strongly inhibits the action of prolyl endopeptidase, and found that the novel compound of the formula [I] to be mentioned later has a specific and strong prolyl endopeptidase inhibitory activity, which resulted in the completion of the invention.

Accordingly, the present invention relates to a compound of the formula

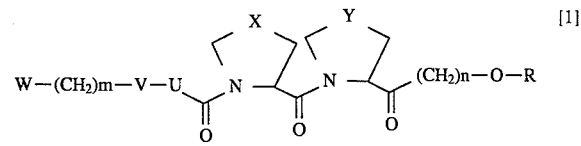

wherein

R is a hydrogen atom or an acyl;

U is —O—, —CHR$^1$— or —NR$^2$— wherein R$^1$ is a hydrogen atom or a hetero ring, and R$^2$ is a hydrogen atom or a lower alkoxycarbonyl lower alkyl;

V is —O—, —S—, —CHR$^3$— or —NR$^4$— wherein R$^3$ is a hydrogen atom or a lower alkoxycarbonyl, and R$^4$ is a hydrogen atom, a lower alkyl or an acyl;

W is methyl, a hetero ring or

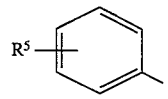

wherein R$^5$ is a hydrogen atom, a halogen atom, a lower alkyl, an amino, a hydroxy or a lower alkoxy;

X and Y are the same or different and each is —CH$_2$— or —S—;

m is an integer of 0 to 6; and n is an integer of 1 to 4, and a pharmaceutically acceptable salt thereof.

The present invention also relates to a pharmaceutical composition useful as a prolyl endopeptidase inhibitor, which comprises, as an active ingredient, a compound of the above-mentioned formula [1] or a pharmaceutically acceptable salt thereof.

Preferable examples of the compounds of the formula [1] include the following.

(1) The compounds of the above-mentioned formula [1] wherein,

R is a hydrogen atom or an acyl;

U is —O—, —CH$_2$— or —NH—;

V is —O—, —S—, —CH$_2$— or —NH—;

W is methyl or

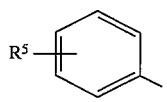

wherein $R^5$ is a hydrogen atom, a halogen atom, a lower alkyl, an amino, a hydroxy or a lower alkoxy;

X and Y are the same or different and each is —$CH_2$— or —S—;

m is an integer of 0 to 6; and n is an integer of 1 to 4, and pharmaceutically acceptable salts thereof.

(2) The compounds of the above-mentioned formula [1] wherein R is a hydrogen atom, acetyl, propionyl, isopropionyl, butyryl, isobutyryl, pivaloyl, benzoyl, phenylacetyl or phenypropionyl, and pharmaceutically acceptable salts thereof.

(3) The compounds of the above-mentioned (1) wherein R is a hydrogen atom, acetyl, propionyl, isopropionyl, butyryl, isobutyryl, pivaloyl, benzoyl, phenylacetyl or phenypropionyl, and pharmaceutically acceptable salts thereof.

The definitions of the respective substituents to be used in the present specification are as follows.

Lower alkyl is a linear or branched alkyl having 1 to 6 carbon atoms, such as methyl, ethyl, propyl, isopropyl, butyl, isobutyl, sec-butyl, tert-butyl, pentyl, isopentyl, neopentyl, tert-pentyl, hexyl, isohexyl and neohexyl. Preferred are linear or branched alkyl having 1 to 4 carbon atoms, which are methyl, ethyl, propyl, isopropyl, butyl, isobutyl, sec-butyl and tert-butyl.

Lower alkoxy is a linear or branched alkoxy having 1 to 6 carbon atoms, such as methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy. Preferred are linear or branched alkoxy having 1 to 4 carbon atoms, which are methoxy, ethoxy, propoxy, isopropoxy, butoxy, isobutoxy, sec-butoxy and tertbutoxy.

Lower alkoxycarbonyl is an alkoxycarbonyl having 2 to 7 carbon atoms, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, isohexyloxycarbonyl and neohexyloxycarbonyl. Preferred are alkoxycarbonyl having 2 to 5 carbon atoms, which are methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl.

Lower alkoxycarbonyl lower alkyl is an alkyl having 1 to 5 carbon atoms and substituted by the aforementioned lower alkoxycarbonyl, which is exemplified by methoxycarbonylmethyl, 2-(methoxycarbonyl)ethyl, 3-(methoxycarbonyl)propyl, ethoxycarbonylmethyl, 2-(ethoxycarbonyl)ethyl, 3-(ethoxycarbonyl)propyl, propoxycarbonylmethyl, 2-(propoxycarbonyl)ethyl and 3-(propoxycarbonyl)propyl.

Acyl is a linear or branched alkanoyl having 1 to 6 carbon atoms, such as formyl, acetyl, propionyl, isopropionyl, butyryl, isobutyryl, pivaloyl, valeryl, isovaleryl, caproyl and isocaproyl; arylcarbonyl having 3 to 11 carbon atoms and optionally having one or more hetero atoms selected from oxygen, nitrogen and sulfur, such as benzoyl, naphthoyl, nicotinoyl, isonicotinoyl, thenoyl, furoyl, pyrrolylcarbonyl, pyrazolylcarbonyl, imidazolylcarbonyl, pyrazinylcarbonyl, pyrimidinylcarbonyl, triazolylcarbonyl, thiazolylcarbonyl, benzofuranylcarbonyl, indolylcarbonyl and benzotriazolylcarbonyl; and arylalkanoyl having 4 to 14 carbon atoms and optionally having one or more hetero atoms selected from oxygen, nitrogen and sulfur, such as phenylacetyl, phenylpropionyl, naphthylacetyl, naphthylpropionyl, pyridylacetyl, thienylacetyl, thienylbutyryl, imidazolylacetyl, thiazolylacetyl, indolylacetyl and indolylpropionyl, with preference given to alkanoyl having 2 to 5 carbon atoms, such as acetyl, propionyl, isopropionyl, butyryl, isobutyryl, pivaloyl, valeryl and isovaleryl; arylcarbonyl having 4 to 7 carbon atoms and optionally having one or more hetero atoms selected from oxygen, nitrogen and sulfur, such as benzoyl, nicotinoyl, isonicotinoyl, thenoyl, furoyl, pyrrolylcarbonyl, pyrazolylcarbonyl, imidazolylcarbonyl, pyrazinylcarbonyl, pyrimidinylcarbonyl and thiazolylcarbonyl; and arylalkanoyl having 5 to 9 carbon atoms and optionally having one or more hetero atoms selected from oxygen, nitrogen and sulfur, such as phenylacetyl, phenylpropionyl, pyridylacetyl, thienylacetyl, thienylbutyryl, imidazolylacetyl and thiazolylacetyl. Particularly preferred are alkanoyl having 2 to 5 carbon atoms, such as acetyl, propionyl, isopropionyl, butyryl, isobutyryl and pivaloyl; arylcarbonyl having 4 to 7 carbon atoms, such as benzoyl; and arylalkanoyl having 5 to 9 carbon atoms, such as phenylacetyl and phenylpropionyl. The aryl ring in the above-mentioned arylcarbonyl and arylalkanoyl may have 1 to 3 substituents, which are exemplified by halogen atom, lower alkyl, amino, hydroxy, lower alkoxy, carboxyl, lower alkoxycarbonyl and acyl.

Halogen atom is chlorine, bromine, fluorine or iodine.

Hetero ring is a saturated or unsaturated 4 to 7-membered ring having 1 to 3 hetero atoms selected from oxygen, nitrogen and sulfur, which are exemplified by pyrrole, furan, thiophene, pyrazole, isoxazole, imidazole, oxazole, thiazole, pyridine, pyrimidine, pyrazine, azetidine, pyrrolidine, tetrahydrofuran, piperidine, piperazine, morpholine and homopiperidine.

Amino-protecting group is a protecting group conventionally used in amino acid chemistry. Any protecting group can be used as long as it protects amino group from various reactions. Examples thereof include tert-butoxycarbonyl (Boc), benzyloxycarbonyl (Cbz), 9-fluorenylmethyloxycarbonyl (Fmoc), trifluoroacetyl, trityl, benzyl and p-methoxybenzyl.

Carboxyl-protecting group forms an ester with carboxyl. Examples thereof are methyl, ethyl, tert-butyl, benzyl, phenacyl, trichloroethyl, p-nitrobenzyl and diphenylmethyl. Any can be used insofar as it is conventionally used in this field and the carboxyl-protecting group is not particularly limited to those exemplified.

Hydroxy-protecting group converts hydroxy into silyl ether, alkyl ether or ester to protect hydroxy from various reactions. Examples of the silyl ether protecting group include trimethylsilyl, tert-butyldimethylsilyl and tert-butyldiphenylsilyl; examples of the alkyl ether protecting group include p-methoxyphenyl, benzyl, p-methoxybenzyl, tert-butyl, trityl, methoxymethyl (MOM), 2-methoxyethoxymethyl (MEM), benzyloxymethyl (BOM) and tetrahydropyranyl (THP); examples of the ester protecting group include acetyl and benzoyl. Any can be used insofar as it is conventionally used in this field and the hydroxy-protecting group is not particularly limited to those exemplified.

Specific examples of —V—U— include —NH—NH—, —NH—$CH_2$—, —$CH_2$—NH—, —$CH_2$—$CH_2$—, —$CH_2$—O—, —S—$CH_2$— and —O—$CH_2$—, with preference given to —NH—$CH_2$—, —$CH_2$—NH—, —$CH_2$—$CH_2$—, —$CH_2$—O—, —S—$CH_2$— and —O—$CH_2$—.

Pharmaceutically acceptable salt is a conventional, non-toxic salt in the field of pharmaceuticals, and exemplified by, but not limited to, inorganic acid addition salts such as hydrochloride, hydrobromide, sulfate, phosphate and nitrate; organic acid addition salts such as acetate, propionate, succinate, glycolate, lactate, malate, tartrate, citrate, maleate, fumarate, methanesulfonate, p-toluenesulfonate and ascorbate; and salts with amino acid such as aspartate and glutamate.

The production methods of the compounds of the formula [1] are explained in the following. While the object compound [1] or its salt can be produced by the production method to be described in the following, the production method of the object compound [1] or its salt is not limited to those described below.

Production method 1

The compound of the formula [6] in the Production method 1 is the same as the compound of the formula [1] wherein n is 1.

mate) in an inert solvent in the presence of a tertiary amine (e.g. pyridine, triethylamine and N-methylmorpholine) at −20° C. to 40° C., and can be used for the reaction with diazomethane or (trimethylsilyl)diazomethane without isolation.

The above-mentioned acid chloride is obtained by reacting the above-mentioned compound [2] with an acid halide (e.g. thionyl chloride and oxalyl chloride) without solvent or in an inert solvent at −20° C. to 40° C. This reaction also proceeds in the presence of a tertiary amine (e.g. pyridine, triethylamine and N-methylmorpholine). The obtained acid chloride can be used for the reaction with diazomethane or (trimethylsilyl)diazomethane without isolation. By inert solvent is meant a solvent which does not interfere with the reaction, hereinafter the same.

Reaction B

A compound of the formula [3] is heated at 50° C.–120° C. in water or a mixed solution of water and a water-soluble solvent (e.g. 1,4-dioxane, tetrahydrofuran, acetone, acetoni-

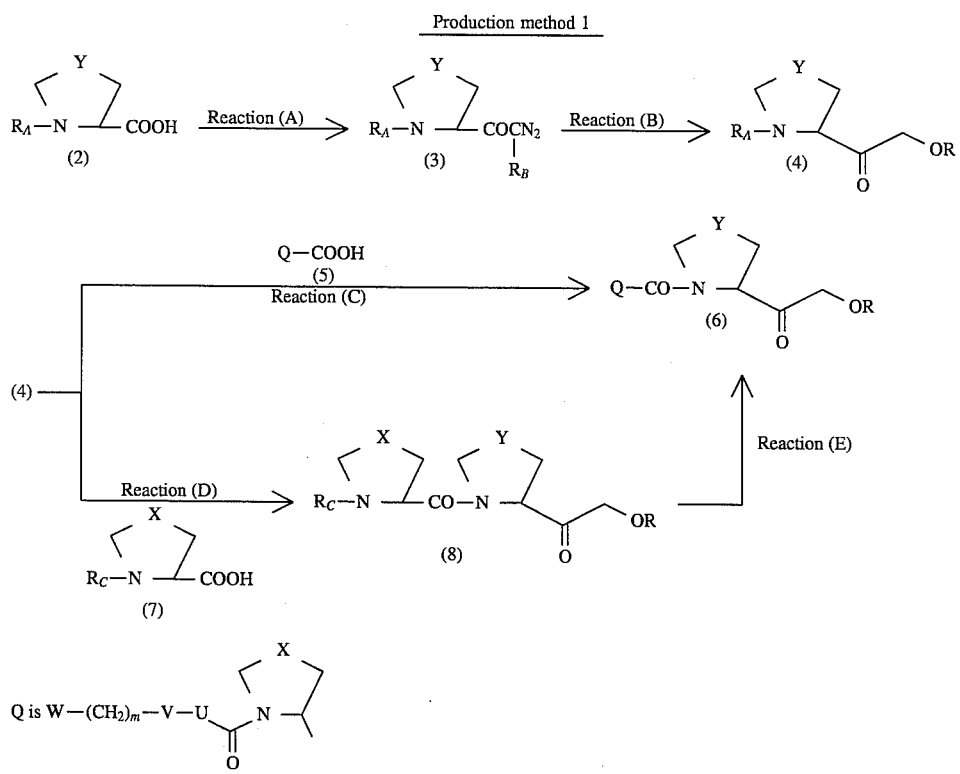

Production method 1 wherein R, W, V, U, X, Y and m are as defined above. $R_A$ and $R_C$ are amino-protecting groups, such as benzyloxycarbonyl, tert-butoxycarbonyl and 9-fluorenylmethyloxycarbonyl. They may be any amino-protecting groups as long as they do not interfere with the reaction. $R_B$ is H or trimethylsilyl.

Reaction (A)

A compound of the formula [2] is converted to the corresponding mixed acid anhydride or acid chloride, which is then reacted with a diazomethane-diethyl ether solution or a (trimethylsilyl)diazomethane-hexane (or methylene chloride) solution, obtainable by a known method, at −20° C. to room temperature, preferably at 0° C. to give a diazoketone [3].

The above-mentioned mixed acid anhydride is obtained by reacting the above-mentioned compound [2] with an acid halide (e.g. pivaloyl chloride and tosyl chloride) or an acid derivative (e.g. ethyl chloroformate and isobutyl chlorofortrile and N,N-dimethylformamide) to give a compound of the formula [4] (R=H). In the present reaction, a copper salt (e.g. copper sulfate, copper chloride and copper acetate), a rhodium salt (e.g. rhodium acetate and rhodium chloride) or a palladium salt (e.g. palladium acetate and palladium chloride) may be used as a catalyst.

Also, a compound of the formula [3] is heated at 50° C.–120° C. in acetic acid to give a compound [4] (R=COCH$_3$). The above-mentioned catalyst may be used in the present reaction.

The compound [4] (R=H) is also obtained by subjecting the above-mentioned compound [4] (R=COCH$_3$) to hydrolysis in water or alcohol (e.g. methanol and ethanol) in the presence of an acid such as hydrochloric acid or a base such as lithium hydroxide, sodium hydroxide, potassium hydroxide, barium hydroxide and potassium carbonate at −20° C. to the refluxing temperature, preferably from 0° C. to room temperature.

The compound [4] (R═H) is reacted according to a known method, namely, with carboxylic acid halide or carboxylic acid anhydride to give an acyl derivative (R═acyl).

Reaction (C)

An amino-protecting group $R_A$ of an intermediate of the formula [4] is removed by a known method and the resulting compound is condensed with a compound of the formula [5] to give an object compound [6].

When the amino-protecting group $R_A$ is, for example, tert-butoxycarbonyl (Boc), an intermediate of the formula [4] is treated with an acid such as hydrobromic acid/acetic acid, hydrochloric acid/1,4-dioxane, formic acid, hydrochloric acid/acetic acid, trifluoroacetic acid and trifluoroacetic acid/acetic acid at −30° C. to 70° C., preferably 0° C. to 30° C. by a conventional method to remove the amino-protecting group $R_A$.

The deprotected compound thus obtained is condensed with a compound [5] by a conventional method to give an object compound [6]. As used herein, Q is a group of the formula

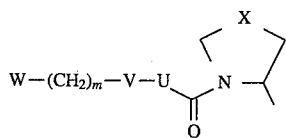

Note that the compound [6] is a compound of the formula [1] wherein n is 1.

This peptide forming reaction can be carried out by a method known per se. Examples of the conventional method include a method comprising the use of a condensing agent such as N,N'-dicyclohexylcarbodiimide (DCC) and water-soluble carbodiimide hydrochloride (1-ethyl-3-(3-dimethylaminopropyl)carbodiimide hydrochloride (EDC.HCl), active ester method, mixed acid anhydride method and acid azide method. The reaction is carried out in an inert solvent at −20° C. to under heating. Suitable solvent is, for example, chloroform, diethyl ether, N,N-dimethylformamide, ethyl acetate, dichloromethane and tetrahydrofuran.

The active ester method comprises reacting the above-mentioned compound [5] with p-nitrophenol, thiophenol, p-nitrothiophenol, N-hydroxysuccinimide and the like in an inert solvent in the presence of DCC to give an active ester such as an ester with N-hydroxysuccinimide, which is reacted with the above-mentioned deprotected compound with or without isolation in an inert solvent at −20° C. to 40° C. to form a peptide bond.

The mixed acid anhydride method comprises reacting the above-mentioned compound [5] with an acid halide (e.g. pivaloyl chloride, tosyl chloride and oxalyl chloride) or an acid derivative (e.g. ethyl chloroformate and isobutyl chloroformate) in an intert solvent in the presence of a tertiary amine (e.g. pyridine and triethylamine) at −20° C. to 40° C. to convert same into a mixed acid anhydride, which is then reacted with the above-mentioned deprotected compound at −20° C. to 40° C. to form a peptide bond.

The method using a condensing agent include reacting the above-mentioned deprotected compound with the compound [5] in an inert solvent in the presence or absence of the above-mentioned tertiary amine such as triethylamine, and with or without the addition of a suitable additive [e.g. 1-hydroxybenzotriazole (HOBt), N-hydroxy-5-norbornene-2,3-dicarboximide (HONB)] using DCC or EDC. HCl as a condensing agent to form a peptide bond.

The acid azide method includes preparing an active ester of the above-mentioned compound [5] in an inert solvent in the same manner as above and adding hydrazine to give a hydrazide. With or without isolation, the obtained hydrazide is converted to an acid azide by reacting same with a nitrite such as tert-butyl nitrite and isoamyl nitrite in an inert solvent in the presence of hydrogen chloride at −70° C. to room temperature, preferably −30° C. to 0° C. The obtained acid azide is then reacted with the above-mentioned deprotected compound at −70° C. to room temperature, preferably −70° C. to 0° C. to form a peptide bond.

Alternatively, the above-mentioned compound [5] is reacted with diphenylphosphoryl azide in an inert solvent in the presence of a tertiary amine such as triethylamine at −30° C. to room temperature to give an acid azide, which is then reacted with the above-mentioned deprotected compound without isolation to form a peptide bond.

The compound [6] (R═H) can be also obtained by subjecting the compound [6] (R═COCH₃) to hydrolysis in water or alcohol (e.g. methanol and ethanol) in the presence of an acid such as hydrochloric acid or a base such as lithium hydroxide, sodium hydroxide, potassium hydroxide, barium hydroxide and potassium carbonate, at −20° C. to the refluxing temperature, preferably at 0° C. to room temperature.

The compound [6] (R═H) is reacted according to a known method, namely, with carboxylic acid halide or carboxylic acid anhydride to give an acyl derivative (R═acyl).

While a compound [6] is prepared by condensing a compound [4] with a compound [5] in Reaction (C), this reaction may be stepwise carried out as in the following. As shown in Reaction (D), a compound [7] of the formula

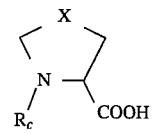

is condensed with the deprotected compound of the formula [4] in the same manner as in the above-mentioned Reaction (C) to give a compound of the formula [8]. The amino-protecting group $R_c$ is removed by a known method as shown in Reaction (E), and the obtained compound is reacted with a compound of the formula W—(CH₂)m—V—U—H (where U is —O— or —NR²—) or a compound of the formula W—(CH₂)m—V—U—COOH (where U is —CHR¹—) to give an object compound [6]. When U in the former case is —O— or —NR²—, for example, W—(CH₂)m—V—U—H is reacted with phosgene, trichloromethyl chloroformate, carbonyldiimidazole and the like in a suitable solvent such as 1,4-dioxane and tetrahydrofuran in the presence of a tertiary amine such as triethylamine at −20° C. to room temperature, and the obtained compound is reacted with a deprotected compound of compound [8] to give a compound [6].

When U is —NH— and V is —CHR³—, W—(CH₂)m—V-N═C═O is reacted with a deprotected compound of compound [8] in a suitable solvent such as methylene chloride, chloroform and N,N-dimethylformamide in the presence or absence of a tertiary amine such as triethylamine at −20° C. to room temperature to give a compound [6].

When U in the latter case is —CHR¹—, a deprotected compound of compound [8] is condensed with W—(CH₂)m—V—U—COOH or the corresponding acid chloride W—(CH₂)m—V—U—COCl by the method in the above-mentioned Reaction (C) to give a compound [6].

Production method 2

The compound of the formula [6] in Production method 2 is the same as the compound of the formula [1] wherein n is 1.

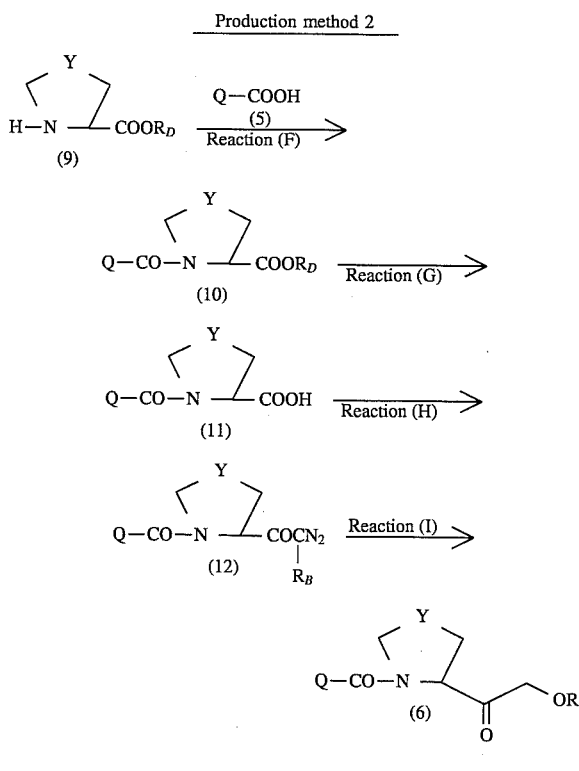

wherein Q, Y, R and Rs are as defined above. $R_D$ is a known carboxyl-protecting group conventionally used.

Reaction (F)

A compound of the formula [9] is reacted with a carboxylic acid of the formula [5] by a conventional method to give a compound [10]. This peptide synthesis reaction is also carried out by a known method described in Reaction (C).

Reaction (G)

A carboxyl-protecting group $R_D$ of the compound of the formula [10] is deprotected by a conventional method to give a compound [11]. When $R_D$ is benzyl, for example, a reductive deprotection with hydrogen in a suitable solvent such as tetrahydrofuran and alcohol (e.g. methanol and ethanol) in the presence of a catalyst conventionally used for catalytic reduction such as palladium-carbon at 0° C. to the refluxing temperature, preferably from room temperature to 50° C., affords a compound [11]. Alternatively, hydrolysis using a base such as lithium hydroxide, sodium hydroxide, potassium hydroxide, barium hydroxide and potassium carbonate in water or an alcohol (e.g. methanol and ethanol) at 0° C. to room temperature affords a compound [11].

Reaction (H)

A diazoketone compound [12] is obtained from the carboxylic acid of the formula [11] by the method described in Reaction (A).

Reaction (I)

The object compound of the formula [6] is obtained from the diazoketone compound of the formula [12] by the method described in Reaction (B).

Production method 3

The compounds of the formulas [6] and [22] in Production method 3 are compounds of the formula [1] wherein n is 1.

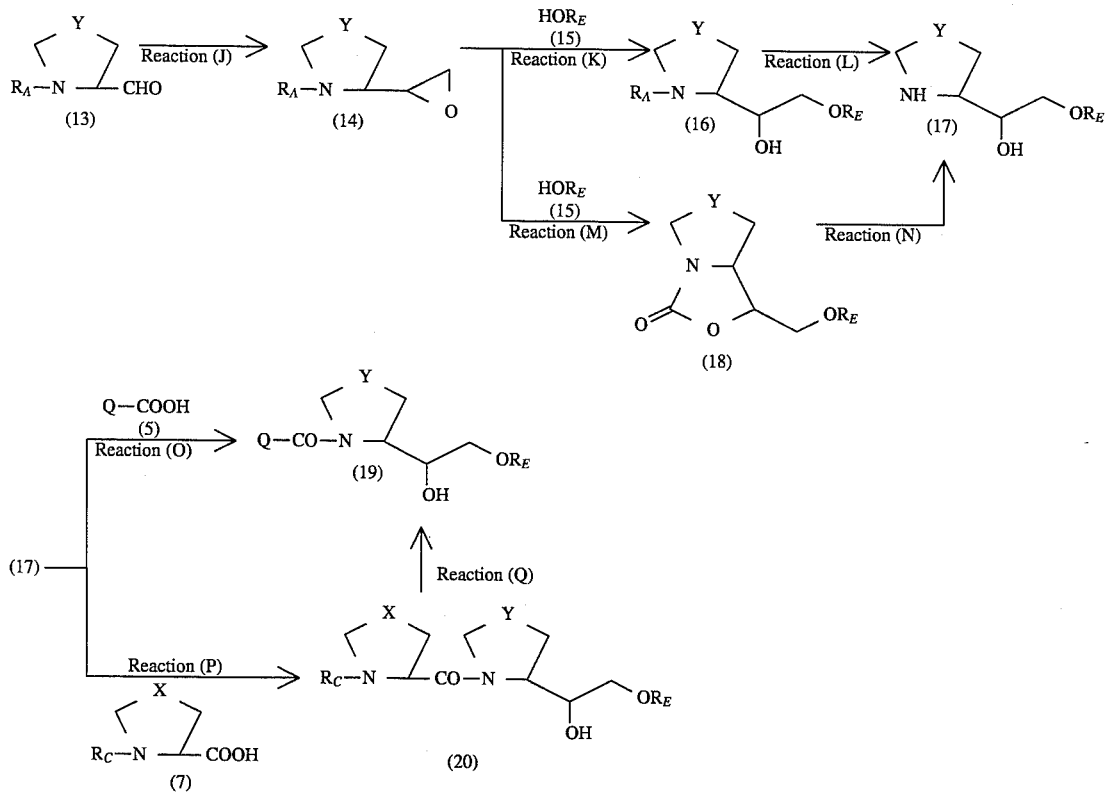

-continued
Production method 3

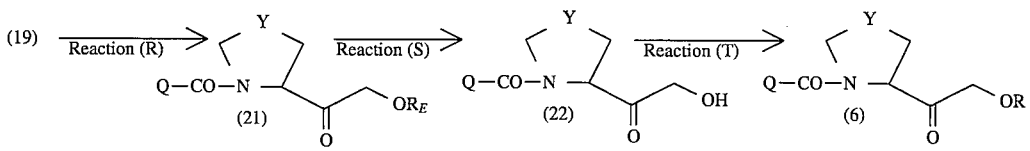

wherein Q, X, Y, R, $R_A$ and $R_C$ are as defined above. $R_E$ is a known hydroxy-protecting group, which does not interfere with the reaction.

Reaction (J)

A compound of the formula [13] is reacted with a sulfur ylide prepared from trimethylsulfonium iodide or trimethylsulfoxonium iodide in the presence of a strong base to give an epoxide of the formula [14]. The reaction is carried out by obtaining a sulfur ylide from the above-mentioned sulfonium salt or sulfoxonium salt using sodium hydridedimethyl sulfoxide, n-butyllithium, sodium bis(trimethylsilyl)amide, potassium tert-butoxide or sodium tert-butoxide in an inert solvent such as tetrahydrofuran, 1,4-dioxane and hexane and reacting the obtained sulfur ylide with a compound of the formula [13]. The reaction is carried out at −70° C. to the refluxing temperature, preferably from −10° C. to room temperature.

The compound [14] is also obtainable by subjecting the compound [13] to a Wittig reaction to convert the compound [13] to an olefin and thereafter converting the obtained olefin to an epoxide with a peroxide. Specifically, methyltriphenylphosphonium halide is reacted with n-butyl lithium in an inert solvent such as tetrahydrofuran and diethyl ether to give the corresponding ylide, which is then reacted with a compound [13] to give an olefin. The reaction is carried out at −70° C. to the refluxing temperature. This olefin is epoxidated using an organic peroxide such as m-chloroperbenzoic acid or an aqueous solution of hydrogen peroxide in a solvent such as methylene chloride, benzene, hexane and methanol at −20° C. to the refluxing temperature, preferably from 0° C. to room temperature to give a compound [14].

Reaction (K)

The present reaction is preferably employed when HO—$R_E$ in the formula [15] is a phenol (e.g. 4-methoxyphenol) and is used in an amount of from 2 equivalents to a large excess. Specifically, sodium methoxide is used in methanol, or sodium hydride is used in a solvent such as 1,4-dioxane and N,N-dimethylformamide to make HO—$R_E$ anion,

after which it is reacted with a compound [14] at room temperature to the refluxing temperature to give an alcohol compound of the formula [16].

Reaction (L)

An amino-protecting group $R_A$ of the compound of the formula [16] is deprotected by the aforementioned Reaction (C) to give a compound of the formula [17].

Reaction (M)

The present reaction is preferably employed when HO—$R_E$ in the formula [15] is an alcohol (e.g. benzyl alcohol and 4-methoxybenzyl alcohol) and is used in an equivalent amount to a large excess, or when an equivalent amount of a phenol (e.g. 4-methoxyphenol) is used. In this case, sodium methoxide is used in methanol, or sodium hydride is used in a solvent such as 1,4-dioxane, N,N-dimethylformamide and 1,3-dimethyl-2-imidazolidinone to make HO—$R_E$ anion,

after which it is reacted with a compound [14] at room temperature to the refluxing temperature to give an alcohol compound of the formula [18].

Reaction (N)

A compound of the formula [18] is reacted with a base such as sodium hydroxide, barium hydroxide and potassium hydroxide in a suitable solvent such as alcohol (e.g. methanol and ethanol) at 0° C. to the refluxing temperature, preferably 0° C. to room temperature to give a compound [17].

Reaction (O)

A compound of the formula [17] is reacted with a compound [5] in the same manner as in peptide forming reaction in the aforementioned Reaction (C) to give a compound of the formula [19].

Also in the preparation of the compound [19], a compound [19] is prepared by converting a compound [17] to a compound of the formula [20] in the same manner as in the aforementioned Reaction (D) [Reaction (P)] and reacted in the same manner as in the aforementioned Reaction (E) [Reaction (Q)].

Reaction (R)

A compound of the formula [19] is treated with a suitable oxidizing agent to give a compound [21]. The present reaction is carried out by, for example, using pyridinium chlorochromate or pyridinium dichromate in an inert solvent such as benzene and N,N-dimethylformamide in the presence or absence of a molecular sieve at 0° C. to the refluxing temperature, preferably at 0° C. to room temperature; using dimethyl sulfoxide in an inert solvent such as methylene chloride in the presence of oxalyl chloride and triethylamine at −80° C. to room temperature; using DCC without or in an inert solvent (e.g. benzene) in the presence of pyridine, trifluoroacetic acid and dimethyl sulfoxide at 0° C. to room temperature; using a sulfur trioxidepyridine complex or diphosphorus pentaoxide without or in an inert solvent (e.g. benzene, toluene and methylene chloride) in the presence of a tertiary amine such as triethylamine and dimethyl sulfoxide at −10° C. to room temperature; or using a hypochlorite (e.g. sodium hypochlorite) in a two-phase solvent such as methylene chloride-water in the presence or absence of 2,2,6,6-tetramethylpiperazine-1-oxide at −20° C. to room temperature, preferably 0° C.

Reaction (S)

When $R_E$ of the compound of the formula [21] is phenyl substituted by alkoxy, a compound of the formula [22] is obtained by oxidative deprotection. For example, when $R_E$ is 4-methoxyphenyl, an object compound [22] is obtained by reacting in a polar solvent such as water, alcohol (e.g. methanol and ethanol), acetonitrile and acetone using oxidizing agent such as ammonium cerium nitrate at −20° C. to the refluxing temperature, preferably room temperature.

When, of the compounds of the formula [21], a compound wherein $R_E$ is an optionally substituted phenylmethyl, namely, a protecting group permitting reductive deprotection, a compound of the formula [22] is obtained by conventional reductive deprotection. For example, when $R_E$ is benzyl, reduction in a suitable solvent such as tetrahydrofuran and alcohols (e.g. methanol and ethanol) in the presence of a catalyst conventionally used for catalytic reduction, such as palladium-carbon using hydrogen or ammonium formate as a hydrogen source at 0° C. to the refluxing temperature under atmospheric pressure to under 200 atm, affords an object compound of the formula [22].
Reaction T A compound of the formula [22] is reacted with a carboxylic acid halide or carboxylic acid anhydride by a known method to give an object compound [6] (R=acyl).
Production method 4

A compound of the formula [28] in Production method 4 is a compound of the formula [1] wherein n is an integer of 3 or 4.

−78° C. to the refluxing temperature, preferably −20° C. to room temperature to give a compound of the formula [24].
Reaction (V)

The compound of the formula [24] is subjected to deprotection of an amino-protecting group $R_A$ as in the aforementioned Reaction (C), and the obtained compound is reacted with a compound of the formula [5] for peptide formation to give a compound of the formula [25].

In the preparation of the compound [25], a compound [24] may be converted to a compound of the formula [26] in the same manner as in the above-mentioned Reaction (D) [Reaction (W)] and reacted in the same manner as in the above-mentioned Reaction (E) to give a compound [25] [Reaction (X)].
Reaction (Y)

The compound of the formula [25] is oxidized in the same manner as in the above-mentioned Reaction (R) to give a compound of the formula [27].
Reaction (Z)

A hydroxy-protecting group $R_F$ of the compound of the formula [27] is deprotected by a conventional method. For

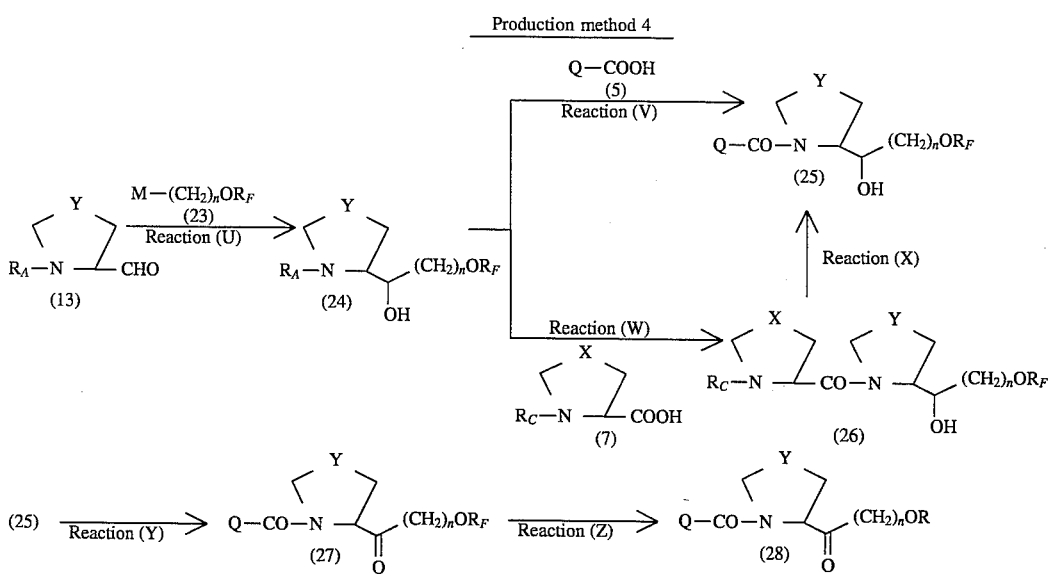

wherein Q, X, Y, R, $R_A$, and $R_C$ are as defined above. n is an integer of 3 or 4, $R_F$ is a known hydroxy-protecting group which does not interfere with the reaction and M is a halogen atom.
Reaction (U)

An alkyl halide of the formula [23] is reacted by a known method, namely, by preparing a Grignard reagent or a reagent equivalent thereto with magnesium, zinc or the like in an inert solvent such as tetrahydrofuran and diethyl ether, and reacting same with a compound of the formula [13] at example, when $R_F$ is benzyl, deprotection in the same manner as in the above-mentioned Reaction (S) affords an object compound [28] (R=H). The compound [28] (R=H) is acylated in the same manner as in the above-mentioned Reaction (T) to give an acyl derivative [28] (R=acyl).
Production method 5

A compound of the formula [36] in Production method 5 is a compound of the formula [1] wherein n is 2.

Production method 5

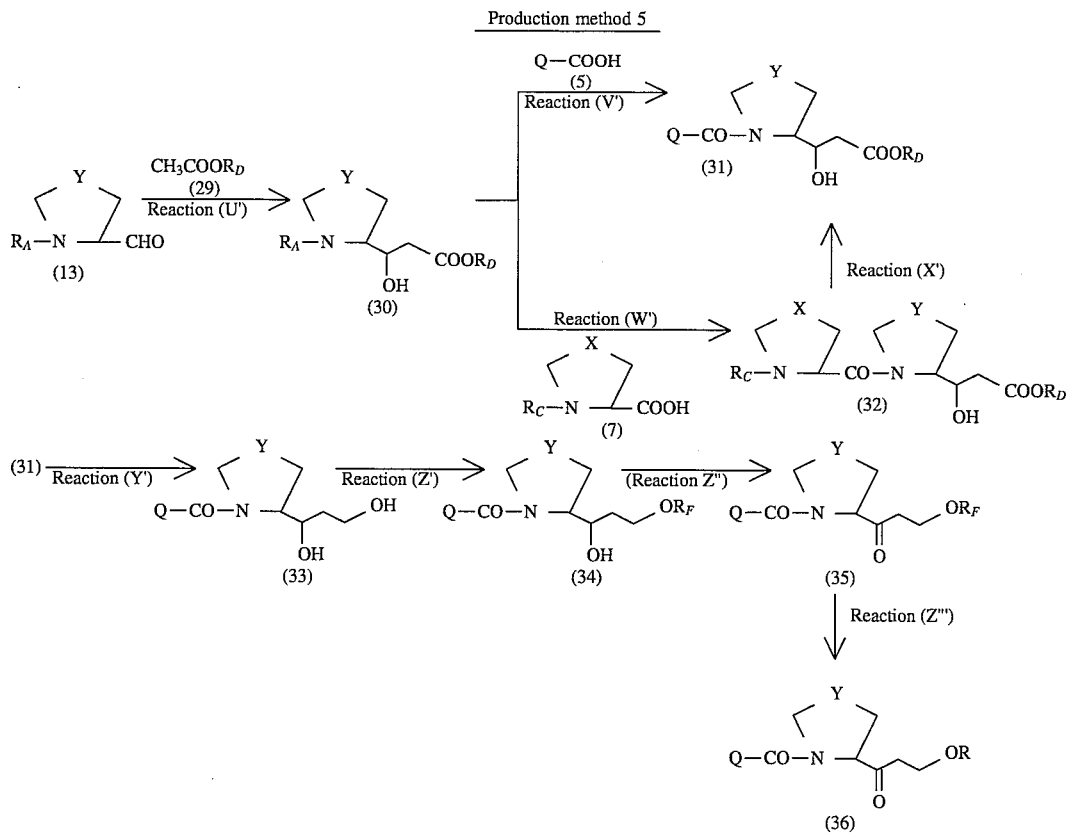

wherein Q, X, Y, R, $R_A$, $R_C$ and $R_D$ are as defined above. $R_F$ is a known hydroxy-protecting group which does not interfere with the reaction.

Reaction (U')

An acetate ester of the formula [29] is reacted with a compound of the formula [13] in the presence of a suitable base to give a compound [30]. The present reaction is carried out by reacting a compound [29] with a suitable base such as lithium diisopropylamide in an inert solvent such as tetrahydrofuran and diethyl ether at −78° C. to room temperature, preferably −78° C. to −20° C. to give a corresponding carbanion. The carbanion is then reacted with a compound [13] at −78° C. to room temperature, preferably −78° C. to −20° C.

Reaction (V')

A compound of the formula [30] is subjected to deprotection of an amino-protecting group $R_A$ as in the aforementioned Reaction (C), and the obtained compound is reacted with a compound of the formula [5] for peptide formation to give a compound of the formula [31].

In the preparation of the compound [31], a compound [30] may be converted to a compound of the formula [32] in the same manner as in the above-mentioned Reaction (D) [Reaction (W')] and reacted in the same manner as in the above-mentioned Reaction (E) to give a compound [31] [Reaction (X')].

Reaction (Y')

The carboxylic ester moiety of the compound of the formula [31] is reduced using a suitable reducing agent to give a compound of the formula [33]. The present reaction is carried out by reducing a compound of the formula [31] in a solvent such as tetrahydrofuran and diglyme using a reducing agent such as lithium borohydride, sodium borohydride and lithium tri-tert-butoxyaluminohydride.

Reaction (Z')

The primary hydroxy of the compound of the formula [33] is protected with a suitable protecting group $R_F$ to give a compound of the formula [34]. For example, when $R_F$ is tert-butyldimethylsilyl, a compound of the formula [34] is obtained by reacting a compound of the formula [33] with tert-butyldimethylsilyl chloride in a solvent such as methylene chloride, acetonitrile and N,N-dimethylformamide in the presence of a base such as triethylamine and pyridine at −20° C. to the refluxing temperature, preferably 0° C. to room temperature.

Reaction (Z")

The compound of the formula [34] is oxidized in the same manner as in the above-mentioned Reaction (R) to give a compound of the formula [35].

Reaction (Z''')

A protecting group $R_F$ of the compound of the formula [35] is deprotected by a conventional method. For example, when $R_F$ is tert-butyldimethylsilyl, the compound of the formula [35] is reacted with tetrabutylammonium fluoride in a solvent such as tetrahydrofuran and acetonitrile at 0° C. to room temperature, or by treating the compound [35] with acetic acid-water or Dowex 50W-X8 (product name, Aldrich Corp.) at 0° C. to 80° C. to give a compound [36] (R═H). The compound [36] (R═H) is acylated in the same manner as in the above-mentioned Reaction (T) to give an acyl derivative [36] (R═acyl).

The compounds to be used as starting materials, N-protected prolines [2] (Y═$CH_2$) and [7] (X═$CH_2$), N-protected thioprolines [2] (Y═S) and [7] (X═S), Q—COOH [5], W—$(CH_2)_m$—V—U—H, W—$(CH_2)_m$—V—U—COOH, ester of proline or thioproline [9], N-protected prolinal [13] (Y═$CH_2$), N-protected thioprolinal [13] (Y═S), HO—$R_E$ [15], compound [23] and compound [29], are all available as substances known per se, or easily derived or synthesized from known precursor substances by a known method.

The compounds [1] thus obtained are isolated and purified from reaction mixtures by an optional method conventionally used in the field of organic synthetic chemistry. For example, they are isolated and purified by column chromatography, solvent extraction, recrystallization and the like. The isolation and purification may be done at every reaction or after some reactions.

The above-mentioned series of compounds respectively have at least 2 asymmetric centers in a molecule. In the present invention, the configuration of each asymmetric center may be R, S or a mixture thereof. The respective optically active compounds are obtained by using an optically active compound as a starting material or by purifying an obtained mixture of stereoisomers by column chromatography, recrystallization and the like.

When the compound of the present invention is used as a pharmaceutical, it is generally administered systemically or locally and orally or parenterally.

While the dose varies depending on age, body weight, symptom, therapeutic effect and administration route, it is 1–100 mg per dose for an adult by single to several times divided oral administrations, or 0.2–20 mg per dose by single to several times divided parenteral administrations.

The compound of the present invention is used in the form of solid composition and liquid composition for oral administration, or injection, suppository and the like for parenteral administration.

The solid preparation for oral administration includes, for example, tablet, pill, capsule, powder and granule. In such a solid composition, one or more active substances are admixed with at least one inactive pharmaceutically acceptable diluent, and excipient, binder, lubricant, disintegrant, solubilizer, stabilizer and the like may be added as necessary. The tablet and pill may be coated with an enteric film where necessary. The capsule includes hard capsule and soft capsule.

The liquid composition for oral administration includes, for example, solution, emulsion, suspension, syrup and elixir. Such liquid composition contains conventionally employed, inactive, pharmaceutically acceptable diluents. Auxiliary agents such as wetting agent and suspension, sweetener, flavor, aromatic agent, preservative and the like may be added as necessary.

The injection for parenteral administration includes, for example, sterile aqeuous or non-aqueous solution, suspension and emulsion. In such injections, one or more active substances are admixed with at least one inactive aqueous, pharmaceutically acceptable diluent or inactive, non-aqueous, pharmaceutically acceptable diluent. Where necessary, an auxiliary such as preservative, wetting agent, emulsifier, dispersing agent, stabilizer and solubilizer may be added. These are generally sterilized by filtration (bacterial removal filter etc.), addition of sterilizing agent or γ-ray irradiation, or by freeze-drying after these treatments to give solid compositions, and used upon, immediately before use, addition of sterile water or sterile diluent for injection.

The present invention is explained in more detail in the following by way of Examples.

The abbreviations used in Examples mean the following.
THF tetrahydrofuran DMF N,N-dimethylformamide
HOBt 1-hydroxybenzotriazole DMSO dimethyl sulfoxide
DMI 1,3-dimethyl-2-imidazolidinone
$^1$H NMR proton nuclear magnetic resonance spectrum
FAB-MS fast atom bombardment mass spectrometry

EXAMPLE 1

(S)-2-[[(S)-2-(Acetoxyacetyl)-1-pyrrolidinyl]carbonyl]-N-(phenylmethyl)-1-pyrrolidinecarboxamide (Compound 1)

a) (S)-1-(tert-Butoxycarbonyl)-2-(diazoacetyl)pyrrolidine

Triethylamine (14.6 ml) and ethyl chloroformate (10.6 ml) were added to a solution of N-(tert-butoxycarbonyl)-L-proline (21.5 g) in THF (330 ml) at −20° C., and the mixture was stirred for 30 minutes. Then, diazomethane (0.6M, diethyl ether solution, 120 ml) was added, and the mixture was stirred overnight. Toluene was added to the reaction mixture, washed with a saturated aqueous solution of sodium bicarbonate and water in order, dried over anhydrous sodium sulfate, and concentrated to give the title compound (26.2 g).

b) (S)-2-(Acetoxyacetyl)-1-(tert-butoxycarbonyl)pyrrolidine (S)-1-(tert-Butoxycarbonyl)-2-(diazoacetyl)pyrrolidine (16.2 g) was dissolved in acetic acid and the mixture was heated at 100° C. for 10 minutes. The reaction mixture was allowed to cool and concentrated under reduced pressure. The residue was dissolved in ethyl acetate, washed with an aqueous solution of sodium bicarbonate and water in order, dried over anhydrous sodium sulfate, and concentrated to give the title compound (8.9 g).

c) (S)-2-[[(S)-2-(Acetoxyacetyl-1-pyrrolidinyl]carbonyl]-N-(phenylmethyl)-1-pyrrolidinecarboxamide (S)-2-(Acetoxyacetyl)-1-(tert-butoxycarbonyl)pyrrolidine (8.9 g) was dissolved in trifluoroacetic acid-acetic acid (1:1 solution, 90 ml), and the mixture was stirred at room temperature for 1.5 hours. The reaction mixture was concentrated under reduced pressure and the residue was suspended in methylene chloride. The suspension was added to a solution of N-(benzylaminocarbonyl)-L-proline obtained by stirring L-proline (4.0 g), benzyl isocyanate (3.9 g) and triethylamine (3.5 g) in DMF (40 ml) at room temperature for 1 hour. Then, HOBt (4.7 g) and water-soluble carbodiimide hydrochloride (6.7 g) were added. The mixture was stirred at room temperature overnight and methylene chloride was added to the reaction mixture. The resulting mixture was washed with 10% potassium hydrogensulfate, a saturated aqueous solution of sodium bicarbonate and water in order, dried over anhydrous sodium sulfate, and concentrated. The residue was dissolved in ethyl acetate, added with active charcoal, stirred at room temperature for 30 minutes, filtered and concentrated to give the title compound (4.8 g) (see Table 1).

EXAMPLE 2

(S)-2-[[(S)-2-(Hydroxyacetyl)-1-pyrrolidinyl]carbonyl]-N-(phenylmethyl)-1-pyrrolidinecarboxamide (Compound 2)

(S)-2-[[(S)-2-(Acetoxyacetyl)-1-pyrrolidinyl]carbonyl]-N-(phenylmethyl)-1-pyrrolidinecarboxamide (3.0 g) obtained in Example 1 was dissolved in water-methanol (1:1, 30 ml) and anhydrous potassium carbonate (1.14 g) were added under ice-cooling. The mixture was stirred at room temperature for 1 hour, and the reaction mixture was concentrated. Methylene chloride was added and the mixture was washed with saturated brine, dried over anhydrous sodium sulfate and concentrated. The residue was dissolved in ethyl acetate, added with active charcoal, stirred at room temperature for 30 minutes, filtered and concentrated to give the title compound (0.81 g) (see Table 1).

EXAMPLE 3

(S)-2-[[(S)-2-(Acetoxyacetyl)-1-pyrrolidinyl]carbonyl]-N-(phenylmethyl)-1-pyrrolidinecarboxamide (Compound 1)

a) N-(Benzylaminocarbonyl)-L-prolyl-L-proline benzyl ester

L-Proline (23.3 g), benzyl isocyanate (22.9 g) and triethylamine (20.5 g) were stirred at room temperature for 1 hour in DMF (250 ml) to give a solution of N-(benzylaminocarbonyl)-L-proline. Thereto were added HOBt (29.7 g), water-soluble carbodiimide hydrochloride (42.13 g), L-proline benzyl ester hydrochloride (48.3 g) and triethylamine (27.9 ml) under ice-cooling, and the mixture was stirred at room temperature for 4 hours. The reaction mixture was poured into ice water and extracted with ethyl acetate. The extract was washed with 10% potassium hydrogensulfate, a saturated aqueous solution of sodium bicarbonate and water in order, dried over anhydrous sodium sulfate, and concentrated to give the title compound (73.6 g).

b) N-(Benzylaminocarbonyl)-L-prolyl-L-proline

Palladium-black (0.87 g) was added to a solution of N-(benzylaminocarbonyl)-L-prolyl-L-proline benzyl ester (43.55 g) in THF (400 ml), and the mixture was stirred at room temperature overnight under a hydrogen atmosphere. The reaction mixture was filtered and concentrated to give the title compound (34.5 g).

c) (S)-2-[[(S)-2-(Diazoacetyl)-1-pyrrolidinyl]carbonyl]-N-(phenylmethyl)-1-pyrrolidinecarboxamide N-(Benzylaminocarbonyl)-L-prolyl-L-proline (6.91 g) was reacted in the same manner as in Example 1-a) to give the title compound (6.90 g).

d) (S)-2-[[(S)-2-(Acetoxyacetyl)-1-pyrrolidinyl]carbonyl]-N-(phenylmethyl)-1-pyrrolidinecarboxamide (S)-2-[[(S)-2-(Diazoacetyl)-1-pyrrolidinyl]carbonyl]-N-(phenylmethyl)-1-pyrrolidinecarboxamide (3.63 g) was dissolved in acetic acid-1,4-dioxane (1:1, 36 ml), and the mixture was heated at 100° C. for 10 minutes. The reaction mixture was concentrated, added with methylene chloride, washed with a saturated aqueous solution of sodium bicarbonate and water in order, dried over anhydrous sodium sulfate, and concentrated. The residue was purified by silica gel column chromatography (eluent: chloroform-methanol) to give the title compound (1.47 g) (see Table 1).

EXAMPLE 4

(S)-2-[[(S)-2-(Hydroxyacetyl)-1-pyrrolidinyl]carbonyl]-N-(phenylmethyl)-1-pyrrolidinecarboxamide (Compound 2)

a) (S)-1-(tert-Butoxycarbonyl)-2-(1,2-epoxyethyl)pyrrolidine

DMI (350 ml) was added to a THF solution (1M, 350 ml) of sodium bis(trimethylsilyl)amide. After cooling the mixture to −13° C., a solution of N-(tert-butoxycarbonyl)-L-prolinal (57.71 g) and trimethylsulfonium iodide (73.9 g) in DMSO (350 ml) was dropwise added, and the mixture was stirred for 1 hour. The reaction mixture was poured into ice water and extracted with toluene. The extract was washed with 10% citric acid, a saturated aqueous solution of sodium bicarbonate and water in order, dried over anhydrous sodium sulfate, and concentrated. The residue was purified by silica gel column chromatography (eluent: hexane-ethyl acetate) to give a mixture (52.74 g) of two diastereomers of the title compound.

b) (S)-1-(tert-Butoxycarbonyl)-2-[1-hydroxy-2-(p-methoxyphenoxy)ethyl]pyrrolidine (S)-1-(tert-Butoxycarbonyl)-2-(1,2-epoxyethyl)pyrrolidine (10.0 g) was added to a mixed solution of p-methoxyphenol (11.64 g) and a solution of sodium methoxide in methanol (1M, 47 ml), and the mixture was stirred at 75° C. for 14 hours under heating. The reaction mixture was poured into water and extracted with toluene. The extract was washed with 10% sodium hydroxide and water in order, dried over anhydrous sodium sulfate, and concentrated. The residue was purified by silica gel column chromatography (eluent: hexane-ethyl acetate) to give the title compound (8.20 g).

c) (S)-2-[[(S)-2-(Hydroxy-2-(p-methoxyphenoxy)ethyl]-1-pyrrolidinyl]carbonyl]-N-(phenylmethyl)-1-pyrrolidinecarboxamide 4N Hydrochloric acid (1,4-dioxane solution, 50 ml) was added to (S)-1-(tert-butoxycarbonyl)-2-[1-hydroxy-2-(p-methoxyphenoxy)ethyl]pyrrolidine (8.03 g), and the mixture was stirred at room temperature for 30 minutes. The reaction mixture was concentrated and the residue was reacted, in the same manner as in Example 3-a), with N-(benzylaminocarbonyl)-L-proline obtained by stirring L-proline (2.63 g), benzyl isocyanate (2.58 g) and triethylamine (2.31 g) in DMF (25 ml) at room temperature for 1 hour to give the title compound (6.31 g).

d) (S)-2-[[(S)-2-[(p-Methoxyphenoxy)acetyl]-1-pyrrolidinyl]carbonyl]-N-(phenylmethyl)-1-pyrrolidinecarboxamide (S)-2-[[(S)-2-[1-Hydroxy-2-(p-methoxyphenoxy)ethyl]-1-pyrrolidinyl]carbonyl]-N-(phenylmethyl)-1-pyrrolidinecarboxamide (5.00 g) was dissolved in methylene chloride (40 ml) and DMSO (20 ml). The mixture was cooled to −18° C. and added with diphosphorus pentaoxide (6.09 g). After stirring for 90 minutes, the reaction mixture was poured into 1.5N aqueous solution of hydrochloric acid and extracted with methylene chloride. The extract was washed with a saturated aqueous solution of sodium bicarbonate and water in order, dried over anhydrous sodium sulfate, and concentrated. The residue was dissolved in ethyl acetate and the mixture was left standing at room temperature for a day to give the title compound (3.83 g).

e) (S)-2-[[(S)-2-(Hydroxyacetyl)-1-pyrrolidinyl]carbonyl]-N-(phenylmethyl)-1-pyrrolidinecarboxamide (S)-2-[[(S)-2-[(p-Methoxyphenoxy)acetyl]-1-pyrrolidinyl] -carbonyl]-N-(phenylmethyl)-1-pyrrolidinecarboxamide (500 mg) was dissolved in acetonitrile (8 ml) and water (2 ml), and thereto were added pyridine (0.22 ml) and ammonium cerium nitrate (1.47 g). The mixture was stirred at room temperature for 30 minutes. The mixture was poured into ice water and extracted with methylene chloride. The extract was dried over anhydrous sodium sulfate, and concentrated under reduced pressure. The residue was purified by silica gel column chromatography (eluent: chloroform-methanol) to give the title compound (203 mg) (see Table 1).

EXAMPLE 5

(S)-2-[[(S)-2-(Hydroxyacetyl)-1-pyrrolidinyl]carbonyl]-N-(phenylmethyl)-1-pyrrolidinecarboxamide (Compound 2)

a) (S)-2-[1-Hydroxy-2-(phenylmethyloxy)ethyl]pyrrolidine

Benzyl alcohol (347 ml) was added to a suspension of sodium hydride (60% dispersion in oil, 89.6 g) in DMI (2.0 l), and the mixture was stirred at 60° C. for 1 hour. A solution of (S)-1-(tert-butoxycarbonyl)-2-(1,2-epoxyethyl)pyrrolidine (478.4 g) obtained in Example 4-a), in DMI (150 ml) was dropwise added, and the mixture was stirred at said temperature for 2 hours. The reaction mixture was poured into a saturated aqueous solution of potassium hydrogensulfate and the mixture was extracted with toluene. The organic layer was washed with water, dried over anhydrous sodium sulfate and concentrated. The residue (547.9 g) was dissolved in ethanol (3.0 l) and a 30% aqueous solution (1 l) of potassium hydroxide was added. The mixture was stirred at 76° C. for 3 hours. The reaction mixture was concentrated, acidified with 1.2N hydrochloric acid and washed with ethyl acetate. The aqueous layer was made basic with 10% sodium hydroxide and extracted with methylene chloride. The extract was dried over anhydrous sodium sulfate, and concentrated to give the title compound (178.2 g).

b) (S)-2-[[(S)-2-(1-Hydroxy-2-(phenylmethyloxy)ethyl]-1-pyrrolidinyl]carbonyl]-N-(phenylmethyl)-1-pyrrolidinecarboxamide Diphenylphosphoryl azide (259.2 g), triethylamine (80.8 g) and (S)-2-[1-hydroxy-2-(phenylmethyloxy)ethyl]pyrrolidine (176.6 g) were added to a solution of N-(benzylaminocarbonyl)-L-proline obtained by stirring L-proline (91.9 g), benzyl isocyanate (90.3 g) and triethylamine (80.8 g) in DMF (900 ml) at room temperature for 1 hour, and the mixture was stirred at room temperature overnight. The reaction mixture was poured into a 7% aqueous solution of citric acid and extracted with ethyl acetate. The extract was washed with water, saturated sodium hydrogenbicarbonate and water in order, dried over sodium sulfate, and concentrated to give the title compound (330.9 g).

c) (S)-N-(Phenylmethyl)-2-[[(S)-2-[(phenylmethyloxy)acetyl]-1-pyrrolidinyl]carbonyl]-1-pyrrolidinecarboxamide The title compound (124.5 g) was obtained from (S)-2-[[(S)2-[1-hydroxy-2-(phenylmethyloxy)ethyl]-1-pyrrolidinyl]carbonyl]-N-(phenylmethyl)-1-pyrrolidinecarboxamide (330.9 g) in the same manner as in Example 4-d).

d) (S)-2-[[(S)-2-(Hydroxyacetyl)-1-pyrrolidinyl]carbonyl]-N-(phenylmethyl)-1-pyrrolidinecarboxamide (S)-N-(Phenylmethyl)-2-[[(S)-2-[(phenylmethyloxy)acetyl]-1-pyrrolidinyl]carbonyl]-1-pyrrolidinecarboxamide (40.0 g) was dissolved in a mixed solvent of methanol (200 ml), water (40 ml) and acetic acid (20 ml). Palladium-black (4.0 g) was added and the mixture was stirred at room temperature under a hydrogen atmosphere for 3.5 hours. The catalyst in the reaction mixture was filtered off and the filtrate was concentrated to give the title compound (25.8 g).

EXAMPLE 6

(S)-2-[[(S)-2-[(Benzoyloxyacetyl)-1-pyrrolidinyl]carbonyl]-N-(phenylmethyl)-1-pyrrolidinecarboxamide (Compound 3)

Benzoyl chloride (0.43 ml) was added, under ice-cooling, to a pyridine solution (12.6 ml) of (S)-2-[[(S)-2-(hydroxyacetyl)1-pyrrolidinyl]carbonyl]-N-(phenylmethyl)-1-pyrrolidinecarboxamide (1.27 g) obtained in Example 5 and the mixture was stirred for 45 minutes. The reaction mixture was diluted with methylene chloride, and the mixture was washed with saturated potassium hydrogensulfate, saturated sodium hydrogencarbonate and water in order, dried over anhydrous sodium sulfate, and concentrated to give the title compound (1.09 g) (see Table 1).

EXAMPLE 7

(S)-N-(Phenylmethyl)-2-[[(S)-2-(pivaloyloxyacetyl)-1-pyrrolidinyl]carbonyl]-1-pyrrolidinecarboxamide (Compound 4)

Triethylamine (0.59 ml), pivaloyl chloride (0.43 ml) were added, under ice-cooling, to a methylene chloride solution (25 ml) of (S)-2-[[(S)-2-(hydroxyacetyl)-1-pyrrolidinyl]carbonyl]-N-(phenylmethyl)-1-pyrrolidinecarboxamide (1.26 g) obtained in Example 5 and the mixture was stirred for 17 hours. The reaction mixture was poured into 5% potassium hydrogensulfate and extracted with methylene chloride. The extract was washed with saturated sodium hydrogencarbonate and water in order, dried over anhydrous sodium sulfate, and concentrated. The residue was purified by silica gel column chromatography (eluent: chloroform-methanol) to give the title compound (1.21 g) (see Table 1).

EXAMPLE 8

(S)-2-[[(S)-2-(Hydroxyacetyl)-1-pyrrolidinyl]carbonyl]-N-(2-phenylethyl)-1-pyrrolidinecarboxamide (Compound 5)

a) (S)-1-[N-(tert-Butoxycarbonyl)-L-prolyl]-2-[1-hydroxy-2(phenylmethyloxy)ethyl]pyrrolidine N-(tert-Butoxycarbonyl)-L-proline (2.93 g), HOBt (4.55 g) and water-soluble carbodiimide hydrochloride (2.88 g) were added to a methylene chloride suspension (30 ml) of (S)-2-[1-hydroxy–2(phenylmethyloxy)ethyl]pyrrolidine (3.00 g) obtained in Example 5a), and the mixture was stirred at room temperature for 14 hours. The reaction mixture was washed with 5% citric acid, saturated sodium hydrogencarbonate and water in order, dried over anhydrous sodium sulfate, and concentrated to give the title compound (4.99 g).

b) (S)-2-[1-Hydroxy-2-(phenylmethyloxy)ethyl]-1-(L-prolyl)-pyrrolidine hydrochloride (S)-1-[N-(tert-Butoxycarbonyl)-L-prolyl]-2-[1-hydroxy-2(phenylmethyloxy)ethyl]pyrrolidine (4.99 g) was dissolved in a 3.6N hydrogen chloride–1,4-dioxane solution, and the mixture was left standing at room temperature for 40 minutes. The reaction mixture was concentrated to give the title compound (2.66 g). c) (S)-2-[[(S)-2-(1-Hydroxy-2-(phenylmethyloxy)ethyl]-1-pyrrolidinyl]carbonyl]-N-(2-phenylethyl)-1-pyrrolidinecarboxamide Triethylamine (0.84 ml) and diphenylphosphoryl azide (0.28 ml) were added to a 1,4-dioxane solution (12 ml) of 3phenylpropionic acid (0.45 g), and the mixture was stirred at 110° C. for 1 hour. The reaction mixture was cooled to room temperature and (S)-2-[1-hydroxy-2-(phenylmethyloxy)ethyl]-1-(L-prolyl)pyrrolidine hydrochloride (1.0 g) was added. The mixture was stirred at room temperature for 1 hour. The reaction mixture was diluted with methylene chloride and washed with 5% citric acid, saturated sodium hydrogencarbonate and water in order, dried over anhydrous sodium sulfate, and concentrated to give the title compound (1.34 g).

d) (S)-N-2-(Phenylethyl)-2-[[(S)-2-[(phenylmethyloxy)acetyl]-1-pyrrolidinyl]carbonyl]-1-pyrrolidinecarboxamide The title compound (0.95 g) was obtained from (S)-2-[[(S)2-[1-hydroxy-2-(phenylmethyloxy)ethyl]-1-pyrrolidinyl]carbonyl]-N-(2-phenylethyl)-1-pyrrolidinecarboxamide (1.34 g) in the same manner as in Example 4-d).

e) (S)-2-[[(S)-2-(Hydroxyacetyl)-1-pyrrolidinyl]carbonyl]-N-(2-phenylethyl)-1-pyrrolidinecarboxamide The title compound (0.54 g) was obtained from (S)-N-(2-phenylethyl)-2-[[(S)-2-[(phenylmethyloxy)acetyl]-1-pyrrolidinyl]carbonyl]-1-pyrrolidinecarboxamide (0.94 g) in the same manner as in Example 5-d) (see Table 2).

EXAMPLE 9

(S)-2-[[(S)-2-(Hydroxyacetyl)-1-pyrrolidinyl]carbonyl]-N-[(4methoxyphenyl)methyl]-1-pyrrolidinecarboxamide (Compound 6)

a) (S)-2-[[(S)-2-[1-Hydroxy-2-(phenylmethyloxy)ethyl]-1-pyrrolidinyl]carbonyl]-N-[(4-methoxyphenyl)methyl]-1-pyrrolidinecarboxamide.

The title compound (1.74 g) was obtained in the same manner as in Example 8-c) using p-methoxyphenylacetic acid (0.63 g) instead of 3-phenylpropionic acid.

b) (S)-N-[(4-Methoxyphenyl)methyl]-2-[[(S)-2-[(phenylmethyloxy)acetyl]-1-pyrrolidinyl]carbonyl],1-pyrrolidinecarboxamide The title compound (0.99 g) was obtained from (S)-2-[[(S)2-[1-hydroxy-2-(phenylmethyloxy)ethyl]-1-pyrrolidinyl]carbonyl]-N-[(4-methoxyphenyl)methyl]-1-pyrrolidinecarboxamide (1.74 g) in the same manner as in Example 4-d).

c) (S)-2-[[(S)-2-(Hydroxyacetyl)-1-pyrrolidinyl]carbonyl]-N[(4-methoxyphenyl)methyl]-1-pyrrolidinecarboxamide.

The title compound (0.21 g) was obtained from (S)-N-[(4methoxyphenyl)methyl]-2-[[(S)-2-[(phenylmethyloxy)acetyl]-1-pyrrolidinyl]carbonyl]-1-pyrrolidinecarboxamide (0.99 g) in the same manner as in Example 5-d) (see Table 2).

EXAMPLE 10

(S)-2-[[(S)-2-(Hydroxyacetyl)-1-pyrrolidinyl]carbonyl]-N-[(4methylphenyl)methyl]-1-pyrrolidinecarboxamide (Compound 7)

a) (S)-2-[[(S)-2-(1-Hydroxy-2-(phenylmethyloxy)ethyl]-1-pyrrolidinyl]carbonyl]-N-[(4-methylphenyl)methyl]-1-pyrrolidinecarboxamide.

The title compound (1.68 g) was obtained in the same manner as in Example 8-c), using p-tolylacetic acid (0.57 g) instead of 3-phenylpropionic acid.

b) (S)-N-[(4-Methylphenyl)methyl]-2-[[(S)-2-[(phenylmethyloxy)acetyl]-1-pyrrolidinyl]carbonyl]-1-pyrrolidinecarboxamide.

The title compound (0.96 g) was obtained from (S)-2-[[(S)2-[1-hydroxy-2-(phenylmethyloxy)ethyl]-1-pyrrolidinyl]carbonyl]-N-[(4-methylphenyl)methyl]-1-pyrrolidinecarboxamide (1.68 g) in the same manner as in Example 4-d).

c) (S)-2-[[(S)-2-(Hydroxyacetyl)-1-pyrrolidinyl]carbonyl]-N[(4-methylphenyl)methyl]-1-pyrrolidinecarboxamide The title compound (0.48 g) was obtained from (S)-N-[(4methylphenyl)methyl]-2-[[(S)-2-[(phenylmethyloxy)acetyl]-1-pyrrolidinyl]carbonyl]-1-pyrrolidinecarboxamide (0.96 g) in the same manner as in Example 5-d) (see Table 2).

EXAMPLE 11

(S)-2-[[(S)-2-(Benzoyloxyacetyl)-1-pyrrolidinyl]carbonyl]-N-[(4methylphenyl)methyl]-1-pyrrolidinecarboxamide (Compound 8)

Benzoyl chloride (0.17 ml) was added to a pyridine solution (4.5 ml) of (S)-2-[[(S)-2-(hydroxyacetyl)-1-pyrrolidinyl]carbonyl]-N-[(4-methylphenyl)methyl]-1-pyrrolidinecarboxamide (0.46 g) obtained in Example 10, and the mixture was stirred under ice-cooling for 4 hours. The reaction mixture was poured into saturated potassium hydrogensulfate and extracted with methylene chloride. The extract was washed with saturated sodium hydrogencarbonate and water in order, dried over anhydrous sodium sulfate, and concentrated to give the title compound (0.37 g) (see Table 2).

EXAMPLE 12

(S)-2-[[(S)-2-(Hydroxyacetyl)-1-pyrrolidinyl]carbonyl]-1-[(4methoxyphenyl)oxyacetyl]pyrrolidine (Compound 9)

a) (S)-2-[[(S)-2-[1-Hydroxy-2-(phenylmethyloxy)ethyl]-1-pyrrolidinyl]carbonyl]-1-[(4-methoxyphenyl)oxyacetyl]pyrrolidine In the same manner as in Example 5-b), the title compound (988 mg) was obtained using (4-methoxyphenyl)oxyacetic acid (273 mg) and (S)-2-[1-hydroxy-2-(phenylmethyloxy)ethyl]-1-(L-prolyl) pyrrolidine hydrochloride (586 mg).

b) (S)-1-[(4-Methoxyphenyl)oxyacetyl]-2-[[(S)-2-[(phenylmethyloxy)acetyl]-1-pyrrolidinyl]carbonyl]pyrrolidine.

A sulfur trioxide-pyridine complex (716 mg) was added, under ice-cooling, to a solution of (S)-2-[[(S)-2-(1-hydroxy-2(phenylmethyloxy)ethyl]-1-pyrrolidinyl]carbonyl]-1-[(4methoxyphenyl)oxyacetyl]pyrrolidine (988 mg) in a mixed solvent of toluene (1 ml), DMSO (1.5 ml) and triethylamine (0.7 ml) and the mixture was stirred for 2.5 hours. The reaction mixture was poured into ice water and extracted with ethyl acetate. The extract was washed with a 10% aqueous solution of citric acid, saturated sodium hydrogencarbonate and water in order, dried over anhydrous sodium sulfate, and concentrated. The residue was purified by silica gel column chromatography (eluent: chloroform-methanol) to give the title compound (673 mg).

c) (S)-2-[[(S)-2-(Hydroxyacetyl)-1-pyrrolidinyl]carbonyl]-1-[(4methoxyphenyl)oxyacetyl]pyrrolidine (S)-1-[(4-Methoxyphenyl)oxyacetyl]-2-[[(S)-2[(phenylmethyloxy)acetyl]-1-pyrrolidinyl]carbonyl]pyrrolidine (673 mg) was subjected to the same reaction as in Example 5-d) to give the title compound (478 mg) (see Table 3).

EXAMPLE 13

(S)-1-[(4-Methoxyphenyl)oxyacetyl]-2-[[(S)-2-(pivaloyloxyacetyl)1-pyrrolidinyl]carbonyl]pyrrolidine (Compound 10)

(S)-2-[[(S)-2-(Hydroxyacetyl)-1-pyrrolidinyl]carbonyl]-1-[(4methoxyphenyl)oxyacetyl]pyrrolidine (284 mg) obtained in Example 12 was subjected to the same reaction as in Example 7 to give the title compound (198 mg) (see Table 3).

EXAMPLE 14

(S)-2-[[(S)-2-(Hydroxyacetyl)-1-pyrrolidinyl]carbonyl]-1-octanoylpyrrolidine (Compound 11)

a) (S)-2-[[(S)-2-[1-Hydroxy-2-(phenylmethyloxy)ethyl]-1-pyrrolidinyl]carbonyl]-1-octanoylpyrrolidine In the same manner as in Example 5-b), the title compound (2.66 g) was obtained using octanoic acid (1.08 g) and (S)-2-[1-hydroxy-2-(phenylmethyloxy)ethyl]-1-(L-prolyl)pyrrolidine hydrochloride (2.93 g).

b) (S)-1-Octanoyl–2-[[(S)-2-(phenylmethyloxy)acetyl]-1-pyrrolidinyl]carbonyl]pyrrolidine (S)-2-[[(S)-2-(1-Hydroxy-2-(phenylmethyloxy)ethyl-1-pyrrolidinyl]carbonyl]-1-octanoylpyrrolidine (2.66 g) was subjected to the same reaction as in Example 12-b) to give the title compound (2.16 g).

c) (S)-2-[[(S)-2-(Hydroxyacetyl)-1-pyrrolidinyl]carbonyl]-1-octanoylpyrrolidine (S)-1-Octanoyl–2-[[(S)-2-(phenylmethyloxy)acetyl]-1-pyrrolidinyl]carbonyl]pyrrolidine (1.77 g) was subjected to the same reaction as in Example 5-d) to give the title compound (1.44 g) (see Table 3).

EXAMPLE 15

(S)-2-[[(S)-2-(Acetoxyacetyl)-1-pyrrolidinyl]carbonyl]-1-octanoylpyrrolidine (Compound 12)

Acetic anhydride (0.42 ml) was added, under ice-cooling, to a pyridine solution (2.4 ml) of (S)-2-[[(S)-2-(hydroxyacetyl)1-pyrrolidinyl]carbonyl]-1-octanoylpyrrolidine (1.06 g) obtained in Example 14 and the mixture was stirred at room temperature for 3 hours. The reaction mixture was poured into 1% hydrochloric acid and extracted with ethyl acetate. The extract was washed with 1% hydrochloric acid, water, saturated sodium hydrogencarbonate and water in order, dried over anhydrous sodium sulfate, and concentrated. The residue was purified by silica gel column chromatography (eluent: chloroform-methanol) to give the title compound (1.02 g) (see Table 4).

EXAMPLE 16

(S)-2-[[(S)-2-(Benzoyloxyacetyl)-1-pyrrolidinyl]carbonyl]-1-octanoylpyrrolidine (Compound 13)

(S)-2-[[(S)-2-(Hydroxyacetyl)-1-pyrrolidinyl]carbonyl]-1-octanoylpyrrolidine (176 mg) obtained in Example 14 was subjected to the same reaction as in Example 6 to give the title compound (137 mg) (see Table 4).

EXAMPLE 17

(R)–4-[[(S)-2-(Hydroxyacetyl)-1-pyrrolidinyl]carbonyl]-3(phenylmethyloxycarbonyl)thiazolidine (Compound 14)

a) N-(Benzyloxycarbonyl)-L-thioprolyl-L-proline methyl ester

The title compound (11.84 g) was obtained in the same manner as in Example 5-b), using N-(benzyloxycarbonyl)-L-thioproline (8.02 g) and L-proline methyl ester hydrochloride (5.46 g).

b) N-(Benzyloxycarbonyl)-L-thioprolyl-L-proline

1N Sodium hydroxide (45 ml) was dropwise added to a methanol solution (120 ml) of N-(benzyloxycarbonyl)-L-thioprolyl-L-proline methyl ester (11.84 g) under ice-cooling, and the mixture was stirred at room temperature for 4 hours. The reaction mixture was concentrated and the residue was dissolved in water. The aqueous solution was acidified with concentrated hydrochloric acid under ice-cooling and extracted with chloroform. The extract was washed with water and concentrated to give the title compound (6.47 g).

c) (R)-4-[[(S)-2-(Diazoacetyl)-1-pyrrolidinyl]carbonyl]-3(phenylmethyloxycarbonyl)thiazolidine N-(Benzyloxycarbonyl)-L-thioprolyl-L-proline (1.82 g) was subjected to the same reaction as in Example 1-a) to give a crude title compound (1.94 g).

d) (R)-4-[[(S)-2-(Hydroxyacetyl)-1-pyrrolidinyl]carbonyl]-3(phenylmethyloxycarbonyl)thiazolidine 1,4-Dioxane-water (5 ml-5 ml) was added to the crude (R)-4[[(S)-2-(diazoacetyl)-1-pyrrolidinyl]carbonyl]-3-(phenylmethyloxycarbonyl)thiazolidine (970 mg) and copper sulfate pentahydrate (several mg), and the mixture was heated at 100° C. for 0.5 hour. 1,4-Dioxane was distilled away under reduced pressure and a saturated sodium hydrogencarbonate was added. The mixture was extracted with ethyl acetate. The extract was washed with 10% citric acid and saturated brine in order, dried over anhydrous sodium sulfate, and concentrated. The residue was subjected to silica gel column chromatography (eluent: chloroform - methanol) to give the title compound (92 mg) (see Table 4).

EXAMPLE 18

(S)-2-[[(S)-2-(Acetoxyacetyl)-1-pyrrolidinyl]carbonyl]-N(4-chlorophenylmethyl)-1-pyrrolidinecarboxamide (Compound 15)

a) N-[(4-Chlorophenylmethyl)aminocarbonyl]-L-prolyl-L-proline methyl ester

The title compound (2.07 g) was obtained in the same manner as in Example 8-c), using 4-chlorophenylacetic acid (1.71 g) and L-prolyl-L-proline methyl ester hydrochloride (2.47 g).

b) N-[(4-Chlorophenylmethyl)aminocarbonyl]-L-prolyl-L-proline

N-[(4-Chlorophenylmethyl)aminocarbonyl]-L-prolyl-L-proline methyl ester (2.07 g) was subjected to the same reaction as in Example 17-b) to give the title compound (1.25 g).

c) (S)-N-(4-Chlorophenylmethyl)-2-[[(S)-2-(diazoacetyl)-1-pyrrolidinyl]carbonyl]-1-pyrrolidinecarboxamide N-[(4-Chlorophenylmethyl)aminocarbonyl]-L-prolyl-L-proline (760 mg) was subjected to the same reaction as in Example 1-a) to give the title compound (234 mg).

d) (S)-2-[[(S)-2-(Acetoxyacetyl)-1-pyrrolidinyl]carbonyl]-N(4-chlorophenylmethyl)-1-pyrrolidinecarboxamide (S)-N-(4-Chlorophenylmethyl)-2-[[(S)-2-(diazoacetyl)-1-pyrrolidinyl]carbonyl]-1-pyrrolidinecarboxamide (234 mg) was subjected to the same reaction as in Example 1-b) to give the title compound (24 mg) (see Table 4).

EXAMPLE 19

(S)-2-[[(S)-2-(4-Hydroxy-1-oxobutyl)-1-pyrrolidinyl]carbonyl]-N-(phenylmethyl)-1-pyrrolidinecarboxamide (Compound 16)

a) (S)-1-(tert-Butoxycarbonyl)-2-[1-hydroxy-4-(phenylmethyloxy)butyl]pyrrolidine A THF solution (20 ml) of N-(tert-butoxycarbonyl)-L-prolinal (4.50 g) was dropwise added to a THF solution (30 ml) of 3-(phenylmethyloxy)propyl magnesium chloride prepared from 1-chloro- 3-(phenylmethyloxy)propane (5.00 g), at −78° C. After stirring for 15 minutes, saturated ammonium chloride (10 ml) was added, and the reaction mixture was allowed to reach room temperature. The reaction mixture was poured into water and extracted with ethyl acetate. The organic layer was washed with 10% citric acid, saturated sodium hydrogencarbonate and saturated brine in order, dried over anhydrous magnesium sulfate, and concentrated. The residue was subjected to silica gel column chromatography (eluent: n-hexane-ethyl acetate) to give two stereoisomers (1.89 g of low polar isomer and 3.05 g of high polar isomer).

b) (S)-2-[[(S)-2-[(1-Hydroxy-4-(phenylmethyloxy)butyl]-1-pyrrolidinyl]carbonyl]-N-(phenylmethyl)-1-pyrrolidinecarboxamide 4N Hydrochloric acid (1,4-dioxane solution, 20 ml) was added to (S)-1-(tert-butoxycarbonyl)-2-[1-hydroxy-4(phenylmethyloxy)butyl]pyrrolidine (high polar isomer, 3.00 g) and the mixture was allowed to stand at room temperature for 30 minutes. The reaction mixture was concentrated and the residue was reacted with N-(benzylamincarbonyl)-L-proline obtained by stirring L-proline (0.99 g), benzyl isocyanate (0.97 g) and triethylamine (0.87 g) in DMF (10 ml) at room temperature for 1 hour, in the same manner as in Example 5-b), to give the title compound (2.20 g).

c) (S)-2-[[(S)-2-[1-Oxo-4-(phenylmethyloxy)butyl]-1-pyrrolidinyl]carbonyl]-N-(phenylmethyl)-1-pyrrolidinecarboxamide (S)-2-[[(S)-2-[(1-Hydroxy-4-(phenylmethyloxy)butyl]-1-pyrrolidinyl]carbonyl]-N-(phenylmethyl)-1-pyrrolidinecarboxamide (2.19 g) was subjected to the same reaction as in Example 12-b) to give the title compound (1.62 g).

d) (S)-2-[[(S)-2-(4-Hydroxy-1-oxobutyl)-1-pyrrolidinyl]carbonyl]-N-(phenylmethyl)-1-pyrrolidinecarboxamide (S)-2-[[(S)-2-[1-Oxo-4-(phenylmethyloxy)butyl]-1-pyrrolidinyl]carbonyl]-N-(phenylmethyl)-1-pyrrolidinecarboxamide (1.00 g) was subjected to the same reaction as in Example 5-d) to give the title compound (180 mg) (see Table 5).

EXAMPLE 20

(S)-2-[[(S)-2-(3-Hydroxy-1-oxopropyl)-1-pyrrolidinyl]carbonyl]-N-(phenylmethyl)-1-pyrrolidinecarboxamide (Compound 17)

a) (S)-1-(tert-Butoxycarbonyl)-2-[2-(ethoxycarbonyl)-1-hydroxyethyl]pyrrolidine

A 1.6M n-hexane solution (23.5 ml) of n-butyl lithium was added to a THF solution (5 ml) of diisopropyl amine (5.3 ml) under an argon atmosphere at −40° C., and the mixture was stirred for 5 minutes and 30 minutes under ice-cooling. After cooling to −78° C., ethyl acetate (3.7 ml) was dropwise added, and the mixture was stirred for 15 minutes. A THF solution (18 ml) of N-(tert-butoxycarbonyl)-L-prolinal (4.98 g) was dropwise added at −78° C. and the mixture was stirred for 1.5 hours. Saturated ammonium chloride (20 ml) was added, and the reaction mixture was allowed to reach room temperature. The reaction mixture was poured into water, and extracted with ether. The organic layer was washed with saturated brine, dried over anhydrous sodium sulfate, and concentrated. The residue was subjected to silica gel column chromatography (eluent: n-hexane-ethyl acetate) to give the title compound (5.73 g).

b) (S)-2-[[(S)-2-[2-(Ethoxycarbonyl)-1-hydroxyethyl]-1-pyrrolidinyl]carbonyl]-N-(phenylmethyl)-1-pyrrolidinecarboxamide 4N Hydrochloric acid (1,4-dioxane solution, 50 ml) was added to (S)-1-(tert-butoxycarbonyl)-2-[2-(ethoxycarbonyl)-1-hydroxyethyl]pyrrolidine (5.73 g), and the mixture was stirred for 2 hours. The reaction mixture was concentrated to dryness and the residue was reacted with N-(benzylamincarbonyl)-L-proline obtained by stirring L-proline (1.15 g), benzyl isocyanate (1.13 g) and triethylamine (1.01 g) in DMF (10 ml), at room temperature for 1 hour, in the same manner as in Example 3-a), to give the title compound (3.36 g).

c) (S)-2-[[(S)-2-(1,3-Dihydroxypropyl)-1-pyrrolidinyl]carbonyl]-N-(phenylmethyl)-1-pyrrolidinecarboxamide Lithium chloride (0.678 g) and sodium borohydride (0.605 g) were added to a solution of (S)-2-[[(S)-2-[2-(ethoxycarbonyl)1-hydroxyethyl]-1-pyrrolidinyl]carbonyl]-N-(phenylmethyl)-1-pyrrolidinecarboxamide (3.36 g) in THF-ethanol (1:1, 50 ml), under ice-cooling, and the mixture was stirred at room temperature overnight. The reaction mixture was filtered with suction, and the filtrate was concentrated. The residue was dissolved in chloroform, and poured into ice water for separation. The aqueous layer was saturated with sodium chloride and extracted with chloroform. The combined organic layer was dried over anhydrous sodium sulfate and concentrated. The residue was subjected to silica gel column chromatography (eluent: chloroform-methanol) to give the title compound (2.50 g).

d) (S)-2-[[(S)-2-[3-(tert-Butyldimethylsilyloxy)-1-hydroxypropyl]-1-pyrrolidinyl]carbonyl]-N-(phenylmethyl)-1-pyrrolidinecarboxamide Triethylamine (0.5 ml), 4-dimethylaminopyridine (20 mg) and tert-butyldimethylsilyl chloride (497 mg) were added to a methylene chloride solution (6 ml) of (S)-2-[[(S)-2-(1,3-dihydroxypropyl)–1-pyrrolidinyl]carbonyl]-N-(phenylmethyl)-1-pyrrolidinecarboxamide (1.13 g), and the mixture was stirred at room temperature overnight. The reaction mixture was diluted with chloroform, washed with saturated sodium hydrogencarbonate and saturated brine in order, dried over anhydrous magnesium sulfate, and concentrated. The residue was subjected to silica gel column chromatography (eluent: chloroform-methanol) to give the title compound (1.02 g).

e) (S)-2-[[(S)-2-(3-Hydroxy-1-oxopropyl)-1-pyrrolidinyl]carbonyl]-N-(phenylmethyl)-1-pyrrolidinecarboxamide A sulfur trioxide-pyridine complex (985 mg) was added to a solution of (S)-2-[[(S)-2-[3-(tert-butyldimethylsilyloxy)-1-hydroxypropyl]-1-pyrrolidinyl]carbonyl]-N-(phenylmethyl)-1-pyrrolidinecarboxamide (1.01 g) in a mixture of toluene (2 ml), DMSO (3 ml) and triethyl amine (0.94 ml), under ice-cooling, and the mixture was stirred for 3 hours. The reaction mixture was poured into ice water, and extracted with ethyl acetate. The organic layer was washed with 10% citric acid, water, saturated sodium hydrogencarbonate, 1% hypochlorous acid, and water in order, dried over anhydrous sodium sulfate, and concentrated. The residue was subjected to silica gel column chromatography (eluent: chloroform-methanol) to give (S)-2[[(S)-2-[3-(tert-butyldimethylsilyloxy)-1-oxopropyl]-1-pyrrolidinyl]carbonyl]-N-(phenylmethyl)-1-pyrrolidinecarboxamide (374 mg) and the title compound (280 mg) (see Table 5).

EXAMPLE 21

(R)-4-(3-Hydroxy-1-oxopropyl)–3-[[(S)-1-(phenylmethyloxycarbonyl)-2-pyrrolidinyl]carbonyl]thiazolidine (Compound 18)

a) (R)-3-(tert-Butoxycarbonyl)-4-[2-(ethoxycarbonyl)-1-hydroxyethyl]thiazolidine N-(tert-Sutoxycarbonyl)-L-thioprolinal (14.78 g) was subjected to the same reaction as in Example 20-a) to give the title compound (25.08 g).

b) (R)-4-[2-(Ethoxycarbonyl)-1-hydroxyethyl]-3-[[(S)-1-(phenylmethyloxycarbonyl)-2-pyrrolidinyl]carbonyl]thiazolidine 4N Hydrochloric acid (1,4-dioxane solution, 90 ml) was added to (R)-3-(tert-butoxycarbonyl)-4-[2-(ethoxycarbonyl)-1-hydroxyethyl]thiazolidine (18.13 g) under ice-cooling, and the mixture was stirred at room temperature for 2 hours. The reaction mixture was concentrated to dryness, and the residue was reacted with N-(benzyloxycarbonyl)-L-proline (9.97 g) in the same manner as in Example 3-a) to give the title compound (2.30 g).

c) (R)-4-(1,3-Dihydroxypropyl)-3-[[(S)-1-(phenylmethyloxycarbonyl)-2-pyrrolidinyl]carbonyl]thiazolidine (R)-4-[2-(Ethoxycarbonyl)-1-hydroxyethyl]-3-[[(S)-1-(phenylmethyloxycarbonyl)-2-pyrrolidinyl]carbonyl]thiazolidine (2.30 g) was subjected to the same reaction as in Example 20-c) to give the title compound (1.09 g).

d) (R)-4-[3-(tert-Butyldimethylsilyloxy)-1-hydroxypropyl]-3[[(S)-1-(phenylmethyloxycarbonyl)-2-pyrrolidinyl]carbonyl]thiazolidine (R)-4-(1,3-Dihydroxypropyl)-3-[[(S)-1-(phenylmethyloxycarbonyl)-2-pyrrolidinyl]carbonyl]thiazolidine (1.09 g) was subjected to the same reaction as in Example 20-d) to give the title compound (1.44 g).

e) (R)-4-[3-(tert-Butyldimethylsilyloxy)-1-oxopropyl]-3-[[(S)-1-(phenylmethyloxycarbonyl)-2-pyrrolidinyl]carbonyl]thiazolidine (R)-4-[3-(tert-Butyldimethylsilyloxy)-1-hydroxypropyl]-3[[(S)-1-(phenylmethyloxycarbonyl)-2-pyrrolidinyl]carbonyl]thiazolidine (1.44 g) was subjected to the same reaction as in Example 20-e) to give the title compound (701 mg).

f) (R)-4-(3-Hydroxy-1-oxopropyl)-3-[[(S)-1-(phenylmethyloxycarbonyl)-2-pyrrolidinyl]carbonyl]thiazolidine (R)-4-[3-(tert-Butyldimethylsilyloxy)-1-oxopropyl]-3-[[(S)-1-(phenylmethyloxycarbonyl)-2-pyrrolidinyl]carbonyl]thiazolidine (215 mg) was dissolved in a mixture of acetic acid-THF-water (3:1:1, 3 ml), and the mixture was stirred at room temperature for 3 hours. The reaction mixture was poured into saturated ammonium chloride and extracted with chloroform. The organic layer was washed with water, saturated sodium hydrogencarbonate and saturated brine in order, dried over anhydrous sodium sulfate, and concentrated. The residue was purified by preparative thin-layer chromatography (silica gel, developing solvent: chloroform-methanol) to give the title compound (97 mg) (see Table 5).

Physical and chemical properties of Compounds 1–18 are shown in Tables 1–5.

TABLE 1

| Comp. No. | Structural formula | Property Melting point Optical rotation (CH₃OH) | MS(m/z) | ¹H NMR(CDCl₃, δ value) |
|---|---|---|---|---|
| 1 | (structure: benzyl-NH-C(=O)-pyrrolidine-C(=O)-N-pyrrolidine-C(=O)-CH₂-O-C(=O)-CH₃) | white needle crystals mp 151–152.9° C. [α]_D −152.9° | FAB-MS: 402(M⁺), 231, 203, 91, 70 | 1.9–2.3(8H, m), 2.15(3H, s), 3.32(1H, m), 3.49(1H, m), 3.61(1H, m), 3.88(1H, m), 4.33(1H, m), 4.51(1H, dd, J=14.3, 5.0Hz), 4.59(1H, m), 4.66–4.73(2H, m), 4.75(1H, d, J=16.9Hz), 4.89(1H, d, J=16.9Hz), 7.30(5H, m) |
| 2 | (structure: benzyl-NH-C(=O)-pyrrolidine-C(=O)-N-pyrrolidine-C(=O)-CH₂-OH) | white needle crystals mp 139.7° C. [α]_D −120° | FAB-MS: 359(M⁺), 328, 301, 231, 203, 91 | 1.8–2.3(8H, m), 3.05(1H, t, J=5.1Hz), 3.33(1H, m), 3.49 (1H, m), 3.62(1H, m), 3.93(1H, m), 4.32(1H, dd, J=19.3, 5.1Hz), 4.33(1H, dd, J=14.6, 5.2Hz), 4.46(1H, dd, J=19.3, 5.1Hz), 4.50(1H, dd, J=14.6, 5.9Hz), 4.60 (1H, m), 4.67–4.73(2H, m), 7.30(5H, m) |
| 3 | (structure: benzyl-NH-C(=O)-pyrrolidine-C(=O)-N-pyrrolidine-C(=O)-CH₂-O-C(=O)-phenyl) | white needle crystals mp 153.1–153.5° C. [α]_D −155° | FAB-MS: 464(MH⁺), 231, 203 | 1.93–2.27(8H, m), 3.32(1H, m), 3.50(1H, m), 3.62(1H, m), 3.89(1H, m), 4.33(1H, m), 4.33(1H, dd, J=14.6, 5.0Hz), 4.52(1H, dd, J=14.6, 6.0Hz), 4.64(1H, br.t), 4.70(1H, m), 4.78(1H, m), 4.99(1H, d, J=16.7Hz), 5.12(1H, d, J=16.7Hz), 7.24 – 7.33(5H, m), 7.45(2H, m), 7.58(1H, m), 8.08(2H, m) |
| 4 | (structure: benzyl-NH-C(=O)-pyrrolidine-C(=O)-N-pyrrolidine-C(=O)-CH₂-O-C(=O)-C(CH₃)₃) | white needle crystals mp 166.7–167.7° C. [α]_D −149° | FAB-MS: 444(MH⁺), 231, 203 | 1.25(9H, s), 1.93–2.35(8H, m), 3.32(1H, m), 3.48(1H, m), 3.60(1H, m), 3.87(1H, m), 4.32(1H, dd, J=14.6, 4.9Hz), 4.51(1H, dd, J=14.6, 6.0Hz), 4.57–4.75(3H, m), 4.70(1H, d, J=16.7Hz), 4.85(1H, d, J=16.7Hz), 7.20–7.35(5H, m) |

TABLE 2

| Comp. No. | Structural formula | Property Melting point Optical rotation (CH₃OH) | MS(m/z) | ¹H NMR(CDCl₃, δ value) |
|---|---|---|---|---|
| 5 | | colorless oil | FAB-MS: 374(MH⁺), 245, 70 | 1.80–2.25(8H, m), 2.80(2H, t, J=6.9Hz), 3.08(1H, br.s), 3.18(1H, m), 3.32–3.64(4H, m), 3.92(1H, dt, J=9.5, 6.9Hz), 4.26–4.37(2H, m), 4.44(1H, br.d, J=20.3Hz), 4.62–4.72(2H, m), 7.17–7.33(5H, m) |
| 6 | | white needle crystals mp 130.9–131.6° C. [α]<sub>D</sub> –116° | FAB-MS: 390(MH⁺), 261, 70 | 1.83–2.25(8H, m), 3.06(1H, br.t), 3.30(1H, m), 3.46(1H, m), 3.61(1H, dt, J=9.6, 6.5Hz), 3.79(3H, s), 3.93(1H, dt, J=9.6, 6.8Hz), 4.26(1H, dd, J=14.2, 5.0Hz), 4.31(1H, dd, J=18.9, 5.2Hz), 4.42(1H, dd, J=14.2, 5.8Hz), 4.45(1H, dd, J=18.9, 4.4Hz), 4.52(1H, br.t), 4.65–4.73(2H, m), 6.85 (2H, d, J=8.7Hz), 7.22(2H, d, J=8.7Hz) |
| 7 | | white needle crystals mp 115.2–116.3° C. | FAB-MS: 374(MH⁺), 245, 70 | 1.82–2.30(8H, m), 2.32(3H, s), 3.30(1H, m), 3.47(1H, m), 3.61(1H, dt, J=9.5, 6.5Hz), 3.93(1H, dt, J=9.5, 6.9Hz), 4.28(1H, dd, J=14.1, 4.1Hz), 4.31(1H, d, J=18.9Hz), 4.45 (1H, d, J=18.9Hz), 4.45(1H, dd, J=14.1, 4.8Hz), 4.55(1H, br.t), 4.67–4.73(2H, m), 7.12 (2H, d, J=8.0Hz), 7.19(2H, d, J=8.0Hz) |
| 8 | | white needle crystals mp 162.8–163.4° C. [α]<sub>D</sub> –148° | FAB-MS: 478(MH⁺), 245, 105, 70 | 1.93–2.31(8H, m), 2.32(3H, s), 3.30(1H, m), 3.48(1H, m), 3.62(1H, m), 3.90(1H, m), 4.28(1H, dd, J=14.2, 4.8Hz), 4.46(1H, dd, J=14.2, 5.9Hz), 4.55(1H, br.t), 4.69(1H, m), 4.79(1H, m), 4.99(1H, d, J=16.8Hz), 5.11(1H, d, J=16.8 Hz), 7.12(2H, d, J=8.0Hz), 7.20(2H, d, J=8.0Hz), 7.44 (2H, m), 7.57(1H, m), 8.08(2H, m) |

TABLE 3

| Comp. No. | Structural formula | Property Melting point Optical rotation (CH₃OH) | MS(m/z) | ¹H NMR(CDCl₃, δ value) |
|---|---|---|---|---|
| 9 | (structure: 4-methoxyphenoxy-acetyl-prolyl-prolinol derivative with CH₂OH) | colorless oil [α]$_D$ −98.8° | FAB-MS: 391(MH⁺), 262, 234, 206 | 1.80–2.30(8H, m), 3.44(1H, br.s), 3.60(2H, m), 3.70 (1H, m), 3.76(3H, s), 3.92(1H, dt, J=9.6, 7.0Hz), 4.31 (1H, d, J=19.0Hz), 4.41(1H, d, J=19.0Hz), 4.57(1H, d, J=14.0Hz), 4.64(1H, d, J=14.0Hz), 4.69(2H, dd, J=8.1, 5.2Hz), 6.81(2H, m), 6.88(2H, m) |
| 10 | (structure: 4-methoxyphenoxy-acetyl-prolyl derivative with pivalate ester) | colorless oil [α]$_D$ −128° | FAB-MS: 475(MH⁺), 262, 234, 206 | 1.25(9H, s), 1.95–2.27(8H, m), 3.60(2H, m), 3.70(1H, m), 3.76(3H, s), 3.90(1H, dt, J=9.1, 7.0Hz), 4.57(1H, d, J=13.9Hz), 4.65(1H, d, J=13.9Hz), 4.68(2H, m), 4.69(1H, d, J=16.9Hz), 4.86(1H, d, J=16.9Hz), 6.81(2H, m), 6.88(2H, m) |
| 11 | (structure: octanoyl-prolyl-prolinol with CH₂OH) | colorless oil [α]$_D$ −111° | FAB-MS: 353(MH⁺), 224, 196 | 0.84(3H, t, J=6.9Hz), 1.25(8H, m), 1.60(2H, quintet, J=6.9Hz), 1.85(1H, m), 1.94(2H, m), 2.03(2H, quintet, J=6.9Hz), 2.08–2.33(5H, m), 3.27(1H, br.s), 3.48(1H, m), 3.60(2H, m), 3.92(1H, m), 4.29 (1H, d, J=18.9Hz), 4.40(1H, d, J=18.9Hz), 4.62(1H, dd, J=8.1, 3.7Hz), 4.67(1H, dd, J=8.3, 5.2Hz) |

TABLE 4

| Comp. No. | Structural formula | Property Melting point Optical rotation (CH₃OH) | MS(m/z) | ¹H NMR(CDCl₃, δ value) |
|---|---|---|---|---|
| 12 | (structure: CH₃-(CH₂)₆-C(O)-N-pyrrolidine-C(O)-N-pyrrolidine-C(O)-CH₂-O-C(O)-CH₃) | colorless oil [α]$_D$ −148° | FAB-MS: 395(MH⁺), 224, 196 | 0.85(3H, t, J=6.6Hz), 1.28(8H, m), 1.63(2H, quintet, J=7.4Hz), 1.89–2.17(8H, m), 2.14(3H, s), 2.25(2H, dt, J=4.0, 7.7Hz), 3.46–3.69(3H, m), 3.90(1H, m), 4.66(2H, m), 4.70(1H, d, J=16.9Hz), 4.85(1H, d, J=16.9Hz) |
| 13 | (structure: CH₃-(CH₂)₆-C(O)-N-pyrrolidine-C(O)-N-pyrrolidine-C(O)-CH₂-O-C(O)-Ph) | colorless oil [α]$_D$ −131° | FAB-MS: 457(MH⁺), 224, 196 | 0.87(3H, t, J=6.9Hz), 1.29(8H, m), 1.63(2H, quintet, J=7.2Hz), 1.91–2.39(10H, m), 3.50(1H, dt, J=9.7, 6.8 Hz), 3.64(2H, m), 3.91(1H, m), 4.65(1H, dd, J=7.9, 3.8 Hz), 4.77(1H, dd, J=7.9, 4.3Hz), 4.98(1H, d, J=16.8 Hz), 5.11(1H, d, J=16.8Hz), 7.45(2H, m), 7.58(1H, m), 8.07(2H, m) |
| 14 | (structure: PhCH₂-O-C(O)-N(H)-CH(CH₂SH)-C(O)-N-pyrrolidine-C(O)-CH₂-OH) | colorless oil [α]$_D$ −148° | FAB-MS: 379(MH⁺), 335 | 1.7–2.2(4H, m), 3.12–3.90(5H, m), 4.26–5.20(8H, m), 7.34(5H, m) |
| 15 | (structure: 4-Cl-C₆H₄-CH₂-N(H)-C(O)-N-pyrrolidine-C(O)-N-pyrrolidine-C(O)-CH₂-O-C(O)-CH₃) | colorless oil [α]$_D$ −107° | FAB-MS: 436(MH⁺), 376, 295, 267, 265 237 | 1.86–2.22(8H, m), 2.14(3H, s), 3.33(1H, m), 3.47–3.67(2H, m), 3.82(1H, m), 4.26(1H, dd, J=15.0, 5.5Hz), 4.47(1H, dd, J=15.0, 6.2Hz), 4.62(2H, m), 4.72(1H, d, J=16.9Hz), 4.83(1H, m), 4.87(1H, d, J=16.9Hz), 7.22–7.36(4H, m) |

TABLE 5

| 化合物 | Structural formula | Property Melting point Optical rotation (CH$_3$OH) | MS(m/z) | $^1$H NMR(CDCl$_3$, δ value) |
|---|---|---|---|---|
| 16 | (structure) | white needle crystals mp 119.5–120.5° C. [α]$_D$ −116° | FAB-MS(Pos): 370(M$^+$ −OH) 231, 203 FAB-MS(Neg): 385(M$^+$ −H), 152 | 1.74–2.20(11H, m), 2.56(1H, dt, J=17.3, 6.4Hz), 2.77(1H, dt, J=17.3, 6.9Hz), 3.31(1H, dd, J=14.5, 7.1Hz), 3.48(1H, m), 3.55–3.65(3H, m), 3.88(1H, dt, J=9.5, 7.0Hz), 4.31(1H, dd, J=14.7, 4.7Hz), 4.51(1H, dd, J=14.7, 5.9Hz), 4.62–4.72(3H, m), 7.20–7.37(5H, m) |
| 17 | (structure) | white needle crystals mp 140.6–141.2° C. [α]$_D$ −114° | FAB-MS: 374(MH$^+$), 307, 231, 203, 154 | 1.70(1H, br.s), 1.80(1H, m), 1.92–2.26(7H, m), 2.57(1H, ddd, J=14.9, 7.0, 3.6Hz), 2.83(1H, ddd, J=14.9, 7.1, 3.9Hz), 3.31(1H, dd, J=14.5, 7.5Hz), 3.48(1H, m), 3.63(1H, dt, J=9.6, 6.6Hz), 3.80–4.02 (3H, m), 4.35(1H, dd, J=14.6, 5.3Hz), 4.49(1H, dd, J=14.6, 5.9Hz), 4.60–4.76(3H, m), 7.20–7.37(5H, m) |
| 18 | (structure) | colorless oil [α]$_D$ −114° | FAB-MS: 393(MH$^+$), 349, 160 | 1.80–2.30(5H, m), 2.55–4.00(8H, m), 4.46–5.20(6H, m), 7.25–7.45(5H, m) |

It is needless to say that the present invention is not limited to these Examples. For example, Compounds 19–34 shown in Table 6 can be obtained in the same manner as above and are encompassed in the present invention. In the Table, Me means methyl and Et means ethyl.

TABLE 6

| Com. No. | Structural formula |
|---|---|
| 19 | |
| 20 | |
| 21 | |
| 22 | |
| 23 | |
| 24 | |
| 25 | |
| 26 | |
| 27 | |

TABLE 6-continued

| Com. No. | Structural formula |
|---|---|
| 28 | 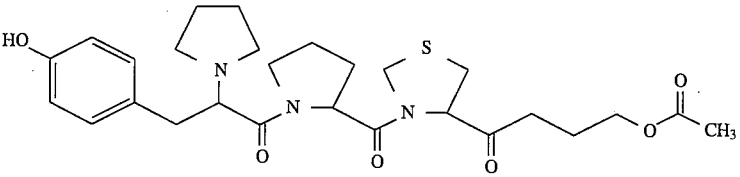 |
| 29 | 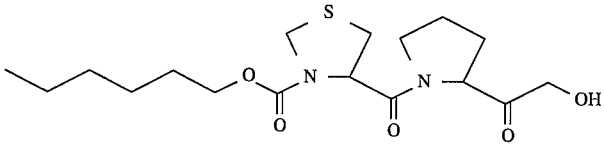 |
| 30 | 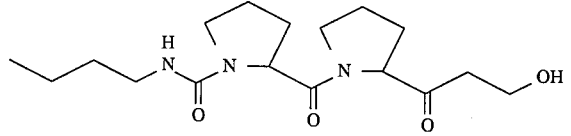 |
| 31 | 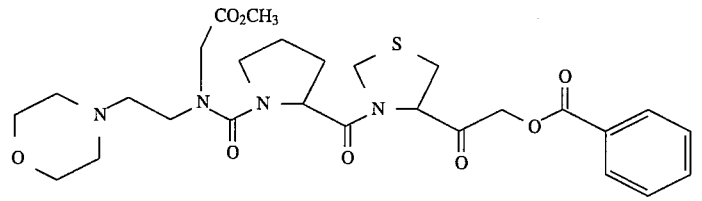 |
| 32 | 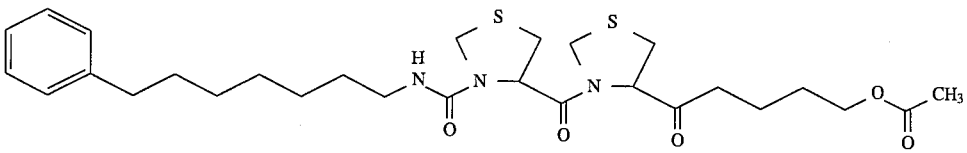 |
| 33 | 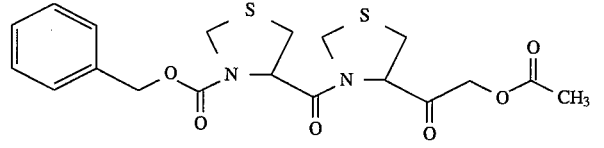 |
| 34 | 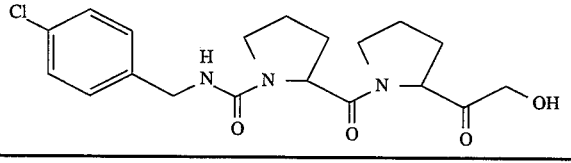 |

The compounds of the present invention of the formula (I) mentioned above were examined for the in vitro prolyl endopeptidase-inhibitory activity and inhibitory activity against various endopeptidases.

EXPERIMENTAL EXAMPLE 1

Prolyl endopeptidase-inhibitory activity

A mixture of a 0.1M potassium-sodium phosphate buffer (pH 7.0, 2675 μl), a solution of the compound of the present invention in a 0.1M potassium-sodium phosphate buffer (pH 7.0, 100 μl) and a solution of prolyl endopeptidase extracted from rat brain in a 25 mM sodium phosphate buffer (100 μl) [123 unit/1, pH 6.8, containing 1 mM dithiothreitol and 0.5 mM EDTA, prepared by the method described in J. Neurochem., 35, 527 (1980)] was preincubated at 30° C. for 30 minutes. Thereto was added a 0.2 mM solution of 7-(N-succinyl-glycyl-prolyl)-4methylcoumarinamide (Peptide Institute, INC.) in a 0.1M potassium-sodium phosphate buffer (pH 7.0, 125 μl), and the mixture was incubated at 30° C. for 1 hour. The reaction mixture was immersed in ice (0° C.) to terminate the reaction, and the fluorescence ($a_1$) was determined ten minutes later (excitation at 370 nm and emission at 440 nm). Concurrently, an experiment wherein, in the above system, the prolyl endopeptidase solution was substituted for a 25 mM sodium phosphate buffer (pH 6.8, containing 1 mM dithiothreitol and 0.5 mM EDTA) and an experiment wherein the solution of the compound of the present invention was substituted for a 0.1M potassium-sodium phosphate buffer (pH 7.0) were conducted. Each fluorescence ($a_2$ and $a_3$) was determined [See *Tanpakushitsu Kakusan Koso*, 29, 127 (1984)]. The prolyl endopeptidase inhibition was calculated by the following formula, and IC$_{50}$, a concentration necessary for 50% inhibition, was estimated by using a semilogarithmic graph paper.

$$\text{Percent inhibition (\%)} = \left(1 - \frac{a_1 - a_2}{a_3 - a_2}\right) \times 100$$

The results are summarized in Table 7.

TABLE 7

| Compound No. | IC$_{50}$ (nM) | Compound No. | IC$_{50}$ (nM) |
|---|---|---|---|
| 1 | 0.1 | 9 | 2 |
| 2 | 0.1 | 10 | 10 |
| 3 | 0.1 | 11 | 0.4 |
| 4 | 1 | 12 | 2 |
| 5 | 0.3 | 13 | 8 |
| 6 | 0.7 | 14 | 1 |
| 8 | 0.4 | 15 | 2 |

As is evident from the test results, the compound of the present invention was confirmed to have superior inhibitory activity against prolyl endopeptidase.

EXPERIMENTAL EXAMPLE 2

Inhibitory activity against various proteases

The compound of the present invention having predetermined concentrations was tested for the specificity of the inhibitory activity against various proteases according to a known test method. As is evident from Table 8, the compound of the present invention was confirmed to specifically inhibit prolyl endopeptidase.

Determination of chymotrypsin-inhibitory activity

In completely the same manner as above, respective fluorescence ($c_1$, $c_2$ and $c_3$) was determined using a 50 mM Tris-HCl buffer (pH 8.0) as a buffer for determination, a 0.2 μM solution of chymotrypsin (derived from bovine pancreas, Sigma) in the same buffer as an enzyme solution, and a 200 μM solution of 7-(N-succinyl-leucyl-leucyl-varyl-tyrosyl)-4-methylcoumarinamide (Peptide Institute, Inc.) in the same buffer as a substrate solution.

Determination of leucine aminopeptidase-inhibitory activity

In completely the same manner as above, respective fluorescence ($d_1$, $d_2$ and $d_3$) was determined using a 50 mM Tris-HCl buffer (pH 8.0) as a buffer for determination, a 0.2 μM solution of leucine aminopeptidase (derived from swine kidney, Sigma) in the same buffer as an enzyme solution and a 200 μM solution of 7-leucyl-4-methyl-coumarinamide (Peptide Institute, Inc.) in the same buffer as a substrate solution.

Determination of elastase-inhibitory activity

In completely the same manner as above, respective fluorescence ($e_1$, $e_2$ and $e_3$) was determined using a 1 mM Tris-HCl buffer (pH 8.5) as a buffer for determination, a 0.2 μM solution of elastase (derived from swine pancreas, Sigma) in the same buffer as an enzyme solution and a 200 μM solution of 7-(N-succinyl-aranyl-prolyl-aranyl)-4-methylcoumarinamide (Peptide Institute, Inc.) in the same buffer as a substrate solution.

Determination of cathepsin B-inhibitory activity

In completely the same manner as above, respective fluorescence ($f_1$, $f_2$ and $f_3$) was determined using a 100 mM sodium phosphate buffer (pH 6.0; containing 1.33 mM

TABLE 8

| Com. No. | Concentration (μM) | Prolyl endo-peptidase | Trypsin | Chymo-trypsin | Leucine amino-peptidase | Elastase | Cathepsin B |
|---|---|---|---|---|---|---|---|
| 1 | 0.1 | 100 | 0 | 0 | 0 | 0 | 0 |
| 2 | 0.1 | 98 | 0 | 0 | 0 | 0 | 0 |
| 3 | 0.1 | 98 | 0 | 0 | 0 | 0 | 0 |
| 4 | 0.1 | 97 | 0 | 0 | 0 | 0 | 0 |
| 5 | 0.1 | 100 | 0 | 0 | 0 | 0 | 0 |
| 6 | 0.1 | 100 | 0 | 0 | 0 | 0 | 0 |
| 8 | 0.1 | 100 | 0 | 0 | 0 | 0 | 0 |

The methods for the determination of the inhibitory activity against various proteases other than prolyl endopeptidase and the method for calculating the inhibition are as follows.

Determination of trypsin-inhibitory activity

In the present invention, a 50 mM Tris-HCl buffer (pH 8.0) was used as a buffer for measurement.

To a mixture of the above-mentioned buffer (850 μl), a solution of the compound of the present invention in the same buffer (50 μl) and a 0.02 μM solution of trypsin (derived from bovine pancreas, Sigma) in the same buffer (50 μl) was added a 200 μM solution of 7-(prolyl-phenylaranyl-arginyl)-4methylcoumarinamide (Peptide Institute, Inc.) in the same buffer (50 μl), and the mixture was incubated at 30° C. for 1 hour. The reaction mixture was immersed in ice (0° C.) to terminate the reaction, and the fluorescence ($b_1$) was determined 1 hour later (excitation at 370 nm and emission at 440 nm). Concurrently, an experiment wherein, in the system above, the trypsin solution was substituted for a buffer and an experiment wherein the solution of the compound of the present invention was substituted for said buffer were conducted. Each fluorescence ($b_2$ and $b_3$) was determined.

EDTA Na$_2$) as a buffer for determination, a 0.02 μM solution of cathepsin B (derived from bovine spleen, Sigma) in the same buffer as an enzyme solution and a 200 μM solution of 7-(N-benzyloxy-carbonyl-phenylaranyl-arginyl)- 4-methyl-couma-rinamide (Peptid Institute, Inc.) in the same buffer as a substrate solution.

Using the fluorescence $x_1$, $x_2$ and $x_3$ wherein x is b, c, d, e or f, measured in the above-mentioned manner, the inhibition against various proteases was calculated by the following formula:

$$\text{Percent inhibition (\%)} = \left(1 - \frac{x_1 - x_2}{x_3 - x_2}\right) \times 100$$

INDUSTRIAL APPLICABILITY

The compound of the formula [I] of the present invention and pharmaceutically acceptable salt thereof exhibit very strong prolyl endopeptidase-inhibitory activity, whereas they do not act on proteases such as trypsin, chymotrypsin, leucine aminopeptidase, elastase and cathepsin B. Accordingly, they are considered to specifically suppress decomposition and inactivation of intracerebral hormones including proline residues, and neurotransmitters such as TRH, substance P, neurotensin, vasopressin and the like. These compounds showed superior anti-amnesia action and learning and memory-improving effects in vitro step-through passive avoidance response tests. Therefore, the compounds of the present invention are expected to contribute to the improvement of the symptoms of various diseases via hormones and neurotransmitters. In addition, they can be used for the prophylaxis and/or treatment of dementia and amnesia including Alzheimer's disease, as an anti-dementia drug or anti-amnesia drug which directly acts on the central symptoms of dementia.

What is claimed is:

1. A compound of the formula

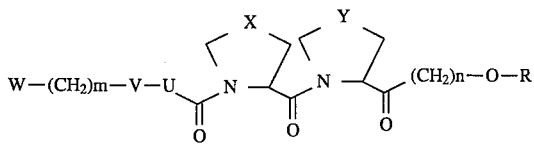

wherein
R is a hydrogen atom or an acyl;
U is —O—, —CHR$^1$— or —NR$^2$— wherein R$^1$ is a hydrogen atom or a hetero ring, and R$^2$ is a hydrogen atom or a lower alkoxycarbonyl lower alkyl;
V is —O—, —S—, —CHR$^3$— or —NR$^4$— wherein R$^3$ is a hydrogen atom or a lower alkoxycarbonyl, and R$^4$ is a hydrogen atom, a lower alkyl or an acyl;
W is methyl, a hetero ring or

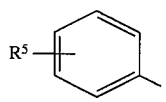

wherein R$^5$ is a hydrogen atom, a halogen atom, a lower alkyl, an amino, a hydroxy or a lower alkoxy;
X and Y are the same or different and each is —CH$_2$— or —S—;
m is an integer of 0 to 6; and
n is an integer of 1 to 4,
or a pharmaceutically acceptable salt thereof.

2. The compound of claim 1 wherein, in the formula,
R is a hydrogen atom or an acyl;
U is —O—, —CH$_2$— or —NH—;
V is —O—, —S—, —CH$_2$— or —NH—;
W is methyl or

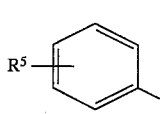

wherein R$^5$ is a hydrogen atom, a halogen atom, a lower alkyl, an amino, a hydroxy or a lower alkoxy;
X and Y are the same or different and each is —CH$_2$— or —S—;
m is an integer of 0 to 6; and
n is an integer of 1 to 4, or a pharmaceutically acceptable salt thereof.

3. The compound of claim 1 wherein R is a hydrogen atom, acetyl, propionyl, isopropionyl, butyryl, isobutyryl, pivaloyl, benzoyl, phenylacetyl or phenypropionyl, or a pharmaceutically acceptable salt thereof.

4. The compound of claim 2 wherein R is a hydrogen atom, acetyl, propionyl, isopropionyl, butyryl, isobutyryl, pivaloyl, benzoyl, phenylacetyl or phenypropionyl, or a pharmaceutically acceptable salt thereof.

5. The compound of claim 1 which is selected from the group consisting of
(1) (S)-2-[[(S)-2-(acetoxyacetyl)-1-pyrrolidinyl]carbonyl]-N-(phenylmethyl)-1-pyrrolidinecarboxamide,
(2) (S)-2-[[(S)-2-(hydroxyacetyl)-1-pyrrolidinyl]carbonyl]-N-(phenylmethyl)-1-pyrrolidinecarboxamide,
(3) (S)-2-[[(S)-2-[(benzoyloxyacetyl)-1-pyrrolidinyl]carbonyl]-N-(phenylmethyl)-1-pyrrolidinecarboxamide,
(4) (S)-N-(phenylmethyl)-2-[[(S)-2-(pivaloyloxyacetyl)-1-pyrrolidinyl]carbonyl]-1-pyrrolidinecarboxamide,
(5) (S)-2-[[(S)-2-(hydroxyacetyl)-1-pyrrolidinyl]carbonyl]-N-(2-phenylethyl)-1-pyrrolidinecarboxamide,
(6) (S)-2-[[(S)-2-(hydroxyacetyl)-1-pyrrolidinyl]carbonyl]-N-[(4-methoxyphenyl)methyl]-1-pyrrolidinecarboxamide,
(7) (S)-2-[[(S)-2-(hydroxyacetyl)-1-pyrrolidinyl]carbonyl]-N-[(4-methylphenyl)methyl]-1-pyrrolidinecarboxamide,
(8) (S)-2-[[(S)-2-(benzoyloxyacetyl)-1-pyrrolidinyl]carbonyl]-N-[(4-methylphenyl)methyl]-1-pyrrolidinecarboxamide,
(9) (S)-2-[[(S)-2-(hydroxyacetyl)-1-pyrrolidinyl]carbonyl]-1[(4-methoxyphenyl)oxyacetyl]pyrrolidine,
(10) (S)-1-[(4-methoxyphenyl)oxyacetyl]-2-[[(S)-2-[(pivaloyloxyacetyl)-1-pyrrolidinyl]carbonyl]pyrrolidine,
(11) (S)-2-[[(S)-2-(hydroxyacetyl)-1-pyrrolidinyl]carbonyl]-1-octanoylpyrrolidine,
(12) (S)-2-[[(S)-2-(acetoxyacetyl)-1-pyrrolidinyl]carbonyl]-1-octanoylpyrrolidine,
(13) (S)-2-[[(S)-2-(benzoyloxyacetyl)-1-pyrrolidinyl]carbonyl]-1-octanoylpyrrolidine,
(14) (R)-4-[[(S)-2-(hydroxyacetyl)-1-pyrrolidinyl]carbonyl]-3-(phenylmethyloxycarbonyl)thiazolidine,
(15) (S)-2-[[(S)-2-(acetoxyacetyl)-1-pyrrolidinyl]carbonyl]-N-(4-chlorophenylmethyl)-1-pyrrolidinecarboxamide,
(16) (S)-2-[[(S)-2-(4-hydroxy-1-oxobutyl)-1-pyrrolidinyl]-carbonyl]-N-(phenylmethyl)-1-pyrrolidinecarboxamide,
(17) (S)-2-[[(S)-2-(3-hydroxy-1-oxopropyl)-1-pyrrolidinyl]-carbonyl]-N-(phenylmethyl)-1-pyrrolidinecarboxamide and
(18) (R)-4-(3-hydroxy-1-oxopropyl)-3-[[(S)-1-(phenylmethyloxycarbonyl)-2-pyrrolidinyl]carbonyl]thiazolidine,
or a pharmaceutically acceptable salt thereof.

6. A pharmaceutical composition comprising a compound of claim 1 or a pharmaceutically acceptable salt thereof, and a pharmaceutically acceptable carrier.

7. A pharmaceutical composition comprising a compound of claim 2 or a pharmaceutically acceptable salt thereof, and a pharmaceutically acceptable carrier.

8. A pharmaceutical composition comprising a compound of claim 3 or a pharmaceutically acceptable salt thereof, and a pharmaceutically acceptable carrier.

9. A pharmaceutical composition comprising a compound of claim 4 or a pharmaceutically acceptable salt thereof, and a pharmaceutically acceptable carrier.

10. A pharmaceutical composition comprising a compound of claim 5 or a pharmaceutically acceptable salt thereof, and a pharmaceutically acceptable carrier.

* * * * *